United States Patent [19]

Borrevang et al.

[11] 3,994,883

[45] Nov. 30, 1976

[54] PENICILLIN AND CEPHALOSPORIN INTERMEDIATES

[75] Inventors: Poul Borrevang, Rodovre; Erling Guddal, Skovlunde; Henning Børge Petersen, Lyngby; Peter Faarup, Frederiksberg; Jørgen Ilum Nielsen, Farum, all of Denmark

[73] Assignee: Novo Industri A/S, Bagsvaerd, Denmark

[22] Filed: Dec. 21, 1973

[21] Appl. No.: 427,363

[30] Foreign Application Priority Data

Dec. 27, 1972 United Kingdom............... 59708/72
Apr. 30, 1973 United Kingdom............... 20526/73
Oct. 8, 1973 United Kingdom............... 46953/73

[52] U.S. Cl.......................... 260/243 C; 260/239.1; 260/306.7 C

[51] Int. Cl.$^2$....................................... C07D 499/02
[58] Field of Search....... 260/239.1, 243 C, 306.7 C

[56] References Cited
FOREIGN PATENTS OR APPLICATIONS
2,218,209   1972   Germany.................... 260/239.1

Primary Examiner—Gerald A. Schwartz
Attorney, Agent, or Firm—Fidelman, Wolffe & Waldron

[57] ABSTRACT

Novel penicillin and cephalosporin intermediates for the synthesis of 6-APA or 7-aminocephem compounds involving formation of a 6 or 7 phosphite amido compound and the conversion of such compound to a desired 6-APA or 7-aminocephem compound.

4 Claims, No Drawings

PENICILLIN AND CEPHALOSPORIN INTERMEDIATES

The present invention relates to novel intermediates for penicillin or cephalosporin synthesis, a method of preparing said intermediates and a method for the preparing of penicillins or cephalosporins or derivatives thereof on the basis of said intermediates.

Numerous methods for the synthesis of penicillins or cephalosporins have been described in the literature. The major part of these syntheses involves the reaction of 6-aminopenicillanic acid (in the following referred to as 6-APA), salts and esters thereof or the corresponding 7-aminocephem compounds with an activated derivative of the acid, with which the amino group is to be acylated.

In one aspect of the invention there is provided a novel intermediate for the synthesis of derivatives of 6-APA or 7-aminocephem compounds in high yields.

The novel intermediate of the invention has the general formula:

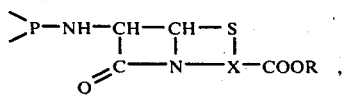

(I)

wherein X is selected from the group consisting of

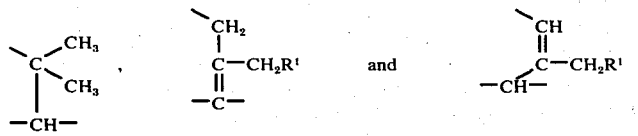

wherein $R^1$ is a hydrogen atom or an acetoxy group, $>P-$ is selected from the group consisting of:

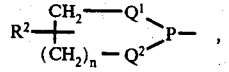

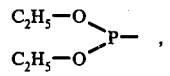

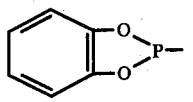

wherein $Q^1$ and $Q^2$ are similar or different and are selected from the group consisting of oxygen and sulphur atoms, $R^2$ is a hydrogen atom or an alkyl group, $n$ is 1 or 2, and R is selected from the group consisting of alkyl, substituted alkyl, aralkyl and substituted aralkyl groups, secondary ammonium, tertiary ammonium groups and metal organic groups.

The compound having the formula I can be prepared by reacting a compound having the formula
>P—Hal,
wherein Hal is a halogen atom and >P— has the meaning defined above with a salt of 6-APA or of 7-aminocephem acid or a derivative of said acids.

A preferred method of preparing the compound having the formula I, may be illustrated by the following reaction scheme:

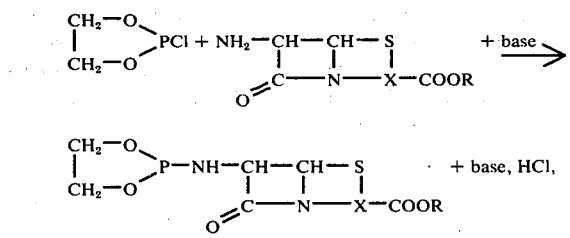

where R and X have the meaning defined above. In case R is a tertiary ammonium group, this reaction is very surprising, since it could be expected that the phosphorous-containing reactant would attack the carboxylic acid group of the molecule and form a mixed anhydride, cf. M. Bodanszky and M. A. Ondetti: Peptide Synthesis, p. 90. However, it has been clearly demonstrated that in the above mentioned reactions the point of attack is the amino group, and only when an excess of the phosphorous-containing reagent is used, the carboxylic acid group is attacked:

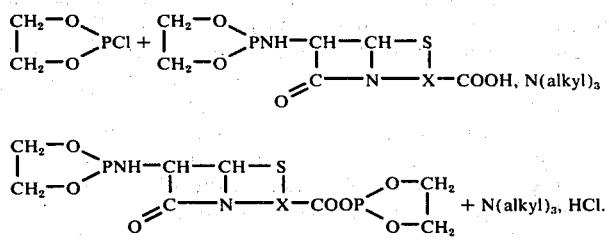

The structure of the compounds having formula I has been established on the basis of their IR and NMR spectra (60 MHz). The spin-spin coupling pattern of the latter shows that the 6α-hydrogen of the 6-APA derivative or the corresponding 7α-hydrogen of the 7-aminocephem derivative is strongly influenced by the introduction of the phosphorous atom.

In 6-APA derivatives with a free $NH_2$-group the proton in the 6-position is normally seen as a doublet at $\delta = 4.4 - 4.6$ ppm ($CDCl_3$). However, as an example in a 6-APA compound having the formula I, cf. Example 1, this proton is found as a multiplet consisting of 8 peaks in the region of $\delta = 4.6 - 5.2$ ppm ($CDCl_3$), from which by first order analysis the following approximate coupling constants can be obtained:

$J_{P-N-C-H}$ : 12 Hz  $J_{H-N-C-H}$ : 6.0 Hz  $J_{H-C-C-H}$ : 4.5 Hz.

The coupling constants $J_{P-N-C-H}$, $J_{H-N-C-H}$ and $J_{H-C-C-H}$ are consistent with those found in literature (for P-N-CH$_3$ compounds are normally found $J_{P-H}$ = 8.5 – 25 Hz (Jackman and Sternhell: Applications of Nuclear Magnetic Resonance Spectroscopy in Organic Chemistry, vol. 5, p. 352 (1969).)). The coupling $J_{H-C-C-H}$ = 4.5 Hz is also found in the signal (doublet) from the proton in the 5-position in 6-APA. This pattern in conjunction with the signal of the 3-hydrogen and the infrared absorption frequencies of the carbonyl group in the 3-position which are consistent with those normally found in 6-APA derivatives, is a conclusive proof for the presence of the structural element:

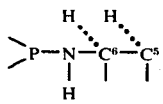

It is even more surprising that a compound having the formula I, wherein R is a secondary ammonium group can be reacted with a halophosphite compound to form the corresponding phosphiteamido compound. However, it has been found that for example 6-aminopenicillanic acid or 7-aminodesacetoxycephalosporanic acid, when dissolved in acetonitrile or chloroform in the presence of two moles of diethylamine reacts with for example ethylene chlorophosphite so as to form in high yield the diethylammonium salt of 6-ethylenephosphiteamidopenicillanic acid or 7-ethylenephosphiteamidodesacetoxycephalosporanic acid and diethylammonium chloride. It might have been expected that ethylene chlorophosphite would react exclusively with the excessive mole of secondary amine.

Examples 5 and 6 set forth the NMR values found during the reaction and prove the progress of the reaction and the configuration of the compounds formed.

The use of secondary ammonium salts are preferred in some cases, because these salts may be more soluble in organic solvents than the corresponding tertiary ammonium salts. This is particularly the case, as far as some 7-aminocephem derivatives are concerned.

The diethylammonium salt of 6-ethylenephosphiteamidopenicillanic acid and the corresponding salt of 7-ethylenephosphiteamidodesacetoxycephalosporanic acid are suitable for the synthesis of penicillins and cephalosporins, respectively.

As activated acid derivative in the preparation of penicillin and cephalosporin compounds from 6-aminopenicillanic acid, 7-aminocephem acid or derivatives thereof, an acid halide is frequently used in the presence of a hydrohalide acceptor.

This method as mentioned in the specifications of Danish applications Nos. 6501/70 and 68/72 suffers from several defects, substantially due to the presence of the added hydrohalide acceptor. The acylation reaction with an α-amino acid halide, hydrohalide is preferably carried out in the absence of any strong base such as alkyl amines.

However, in order to dissolve e.g. 6-aminopenicillanic acid (6-APA) in an organic solvent, it is necessary to use an excess of e.g. triethyl amine per mole of 6-APA. Thus, for the further acylation reaction it may be preferred to remove the excessive alkyl amine but, on the other hand, a hydrohalide acceptor is necessary to promote the reaction.

The best solution of the above mentioned difficulties would apparently be to carry out the acylation reaction without liberation of any hydrohalide at all and, accordingly, without addition of a hydrohalide acceptor. This solution of the mentioned difficulties is achieved by the method of the invention for the preparation of penicillin or cephalosporin derivatives.

The method of the invention comprises the step of reacting a compound having the formula I with a compound having a reactive acyl group.

The preparation of a compound having the formula I and the reaction of said compound with an acid halide as the compound having a reactive acyl group may be illustrated as follows:

To 1 mole of 6-aminopenicillanic acid or 7-aminodesacetoxy-cephalosporanic acid in an organic solvent is added 2 moles of triethylamine or 2 moles of diethylamine. By addition of 1 mole of ethylene chlorophosphite the 6- or 7-ethylenephosphiteamido compound is formed, and simultaneously the excessive amount of amine is converted into the corresponding hydrochloride. Optionally, at this stage of the synthesis, 1 mole of trialkylsilylhalide, 1 mole of ethylene chlorophosphite or 1 mole of a reactive alkyl halide may be added to form the corresponding ester.

1 mole of acid chloride, e.g. phenylglycylchloride, HCl is then added without using a hydrohalide acceptor, since it has been proved by $^{31}$P NMR spectres that the amide formation proceeds with liberation of ethylene chlorophosphite to which under the present conditions the β-lactam ring is inert.

Cyclic N-carboxy anhydrides (Leuchs' anhydrides) have been used for the preparation of α-aminopenicillins (cf. e.g. J. Am. Chem. Soc. 86 (1964) 3870, and DOS 1.942.693, Example 13). The yields, however, are low or moderate, and undesired by-products are formed by reacylation and polymerization of the N-carboxy anhydride. It is difficult to avoid such by-products since the liberated carbamic acid shows a tendency to spontaneous decarboxylation with liberation of the amino group (cf. e.g. M. Bodanszky: Peptide Synthesis). In a basic medium the carbamate ion will not decarboxylate, but in the presence of unreacted anhydride a rapid reacylation will take place via a mixed anhydride (cf. Chem. Pharm. Bull. 20 (1972) 664).

By the method of the present invention penicillins and cephalosporins can be obtained in satisfactory yields by reacting the N-carboxy anhydride with the above mentioned phosphiteamido compounds of the formula I. Without restricting the invention to this theory it is assumed that this is due to a stablization of the liberated carbamic acid in form of a phosphite ester during the reaction.

Among other activated acid derivatives which have been used in the acylation of the amino group of 6-APA or derivatives thereof are various forms of activated esters, e.g. p-nitrophenyl, cyanomethyl esters and the like.

Surprisingly, it has been found that in the method of the present invention even unactivated esters such as silyl esters may react with the above mentioned intermediates having formula I in which R is an alkyl, substituted alkyl, aralkyl or substituted aralkyl group to form penicillins or cephalosporins. Silyl esters possess the advantage that they can be easily prepared.

Few syntheses of penicillin or cephalosporin derivatives are known in which a free carboxylic acid is reacted with a derivative of 6-APA or a 7-aminocephem compound.

The specification of British Patent No. 1.268.536 discloses that 6-isocyanato penicillanic acids may be prepared by reacting phosgene with a 6-APA ester. The 6-isocyanato penicillanic ester may then be reacted with a free acid to yield a penicillin derivative. However, this reaction can only be performed with moderate yield, and furthermore this known synthesis is not fully acceptable because of the use of phosgene which is poisonous and technically difficult to handle.

However, by the method of the invention a compound having the formula I, in which R is an alkyl, substituted alkyl, aralkyl, substituted aralkyl, or a metal organic group can be reacted with a carboxylic acid to form the corresponding penicillin or cephalosporin compound and converting, if necessary, said compound into the desired derivative.

The above reaction can be illustrated by the following reaction scheme, in which a 6-APA derivative of the formula I is reacted with a carboxylic acid:

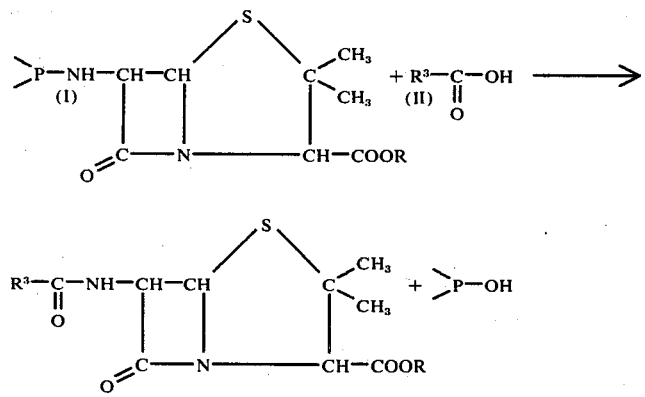

in which R has the meaning defined above, and $R^3$ is an organic group.

Examples of compounds having a reactive acyl group for use in the reaction with a compound having the formula I are compounds containing one of the following acyl groups:

1) 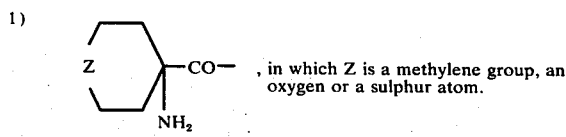, in which Z is a methylene group, an oxygen or a sulphur atom.

2)   3) 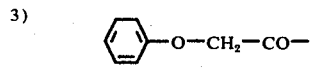

4) 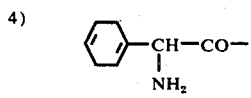  5) 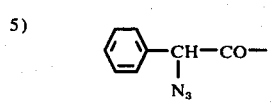

6) 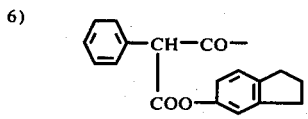  7) 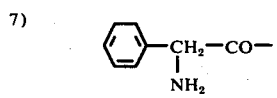

8) 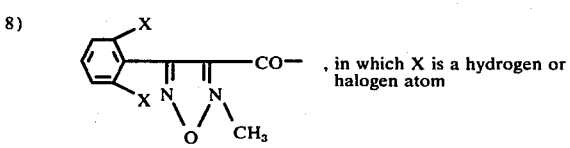, in which X is a hydrogen or halogen atom

9) 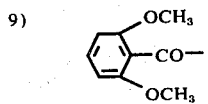

10) -continued
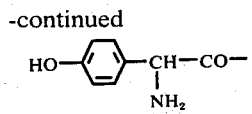

11) 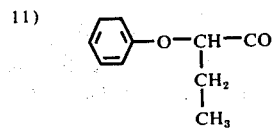

12) 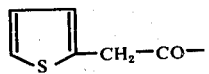

13) 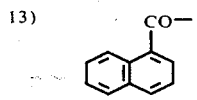

14) 

15) 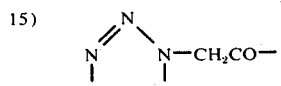

16) 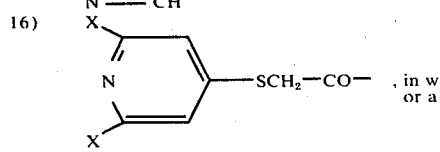, in which X is a hydrogen or a halogen atom

17) N≡C—CH₂—CO—

18) 

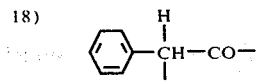

19) 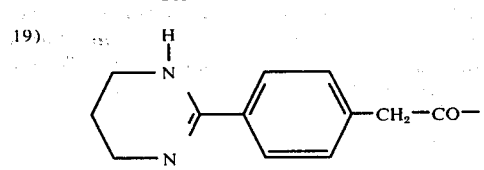

In case these compounds contain one or more amino groups they may be used in the form of a salt, e.g. a hydrochloride. It is also possible to use compounds in which the amino groups have been converted into amide functions. Furthermore, OH groups which may be present in said compounds may be protected in a manner which is well known per se.

A compound of the formula I wherein R is an substituted ammonium group is suitable for the preparation of any ester of penicillin and cephalosporin.

Some of the penicillin esters prepared by said method are valuable antibiotics.

In a further embodiment of the method of the invention phthalide esters of penicillin and cephalosporin can be prepared in high yields from 6-aminopenicillanic acid or 7-aminocephem acids without effecting an epimerization of $C_6$ (or at $C_7$).

This method comprises the steps of coupling a compound having the formula I wherein R is a substituted ammonium group as defined above with a 3-halophthalide to form the corresponding phthalide ester and acylating said ester to form the corresponding penicillin or cephalosporin ester.

The fact that no epimerization takes place has been proved by coupling the trialkylammonium salt of 6-ethylenephosphiteamidopenicillanic acid with 3-bromophthalide in acetonitril and by following the progress of the reaction by means of NMR spectra (60 MHz), cf. Example 30.

The method of the invention is applicable for the preparation of phthalide esters of penicillin or cephalosporin in general. Thus, the esters prepared by said method are not only suitable as antibiotics, but they can also be used as intermediates or auxiliary agents for further synthesis.

Compounds having the general formula I can be prepared in high yields (i.e. 90–100%). Therefore, it is unnecessary to separate said compounds from the reaction medium and the subsequent reactions are carried out in the same reaction medium.

An embodiment of the method of the invention is illustrated by the following reaction scheme:

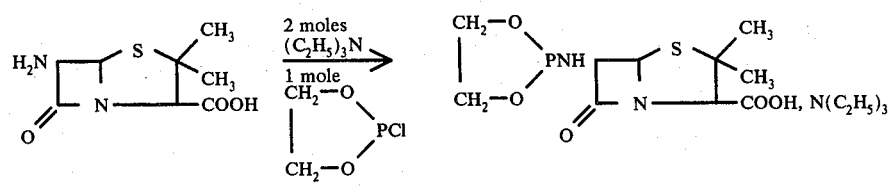

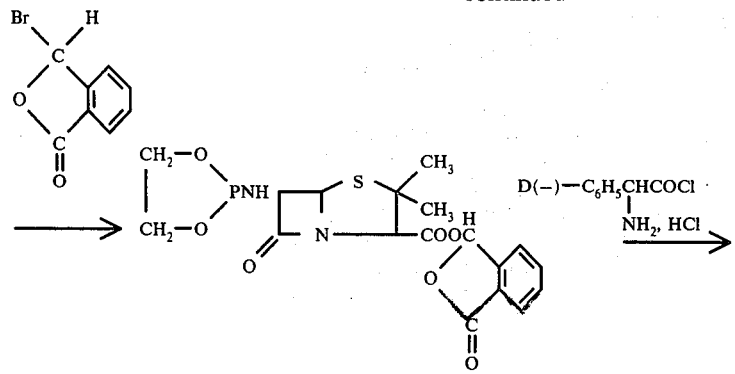 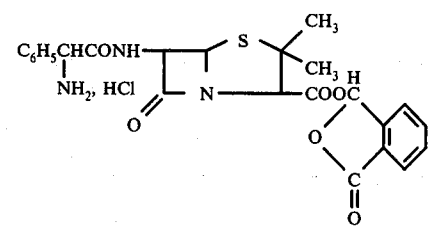

As indicated above, compounds having the formula I, where R is a substituted ammonium group can be acylated directly after being coupled with the 3-bromophthalide with for example D(—)-phenylglycylchloride, HCl, to form the desired penicillin or cephalosporin in a high yield.

The invention will now be described in further detail with reference to the following examples:

EXAMPLE 1

6-Ethylenephosphiteamidopenicillanic acid, triethylammonium salt.

2.1 g (10 millimoles) of 6-aminopenicillanic acid (6-APA) are dissolved in 15.0 ml acetonitrile by addition of 2.8 ml (20 millimoles) of triethylamine, and the solution is then cooled to —40° C. To this solution is added in one portion with stirring and introduction of dry nitrogen a solution of 0.9 ml (10 millimoles) of ethylene chlorophosphite in 5.0 ml acetonitrile cooled to —40° C. After stirring for ½ hour, during which time the temperature of the reaction mixture raised to room temperature, the triethylammoniumchloride formed (1.2 g, 9 millimoles) is filtered off.

The filtrate is cooled to about —25° C, and the crystals thereby formed are filtered. In this way 2.2 g of 6-ethylenephosphiteamidopenicillanic acid, triethylammonium salt is obtained.

The IR spectrum (CHCl$_3$) shows characteristic bands at 1010 cm$^{-1}$ (POC), 1605 cm$^{-1}$ (-COO$^-$) and 1755 cm$^{-1}$ (-CO-, β-lactam). The NMR spectrum (CDCl$_3$) shows characteristic signals at:

| δ ppm | | |
|---|---|---|
| 1.29 (t) | J = 7.5 Hz | (CH$_2$C<u>H</u>$_3$)$_3$ |
| 1.61 (s) <br> 1.63 (s) | | }(2) C$<$ CH$_3$ / CH$_3$ |
| 3.08 (q) | J = 7.5 Hz | (C<u>H</u>$_2$CH$_3$)$_3$ |
| 3.7–4.3 (m) | | <u>H</u>$_2$C—O <br> <u>H</u>$_2$C—O $>$P— |
| 4.29 (s) | | (3) C—<u>H</u> |
| 4.83 (multiplet consisting of 8 peaks) <br> J$_{5,6}$ = 4.4 Hz, J$_{PNCH}$ = 12 Hz, <br> J$_{HNCH}$ = 6.0 Hz | | (6) C—<u>H</u> |
| 5.55 (d) | J$_{5,6}$ = 4.4 Hz | (5) C—<u>H</u> |

When using the ethylenephosphite compound in the preparation of penicillines it is unnecessary to separate the ethylene phosphite compound, because the NMR spectrum of a sample of the reaction mixture after removal of the triethylammonium chloride by filtration shows a content of 90–100% of the theoretical amount of the ethylenephosphite compound.

EXAMPLE 2

6-Diethylphosphiteamidopenicillanic acid, triethylammonium salt.

2.16 g (10 millimoles) of 6-aminopenicillanic acid are dissolved in 10 ml of chloroform by addition of 2.8 ml (20 millimoles) of triethylamine. The solution is cooled to —15° C and 1.57 g (10 millimoles) of diethylchlorophosphite is added dropwise under dry nitrogen. The mixture is stirred 5 minutes at —15° C and is then heated to room temperature and stirred for 45 minutes.

Dry ether is added to the mixture to precipitate the triethylammoniumchloride formed. The salt is filtered off. The filtrate is evaporated to a white wax which is very hygroscopic. The product is stable in cold, dry solution and when stored under dry nitrogen. The product may contain small amounts of unreacted 6-aminopenicillanic acid, triethylammonium salt.

The IR spectrum (CHCl$_3$) shows characteristic bands at 1030 cm$^{-1}$ and 1165 cm$^{-1}$ (P-O-C$_2$H$_5$), 1615 cm$^{-1}$ (COO$^-$), 1770 cm$^{-1}$ (-CO-, β-lactam), 2200–2600 cm$^{-1}$ (ammonium ion: ≡ N$^+$-H) and 3400 cm$^{-1}$ (NH). The NMR spectrum (CDCl$_3$) shows characteristic signals at:

| δ ppm | | |
|---|---|---|
| 1.29 (t) | J = 7.5 Hz | { (O—CH$_2$—C<u>H</u>$_3$)$_2$ <br> (—C<u>H</u>$_2$—CH$_3$)$_3$ |
| 1.62 (s) <br> 1.65 (s) | | }(2) C$<$ CH$_3$ / CH$_3$ |

3,994,883

-continued

| | | |
|---|---|---|
| 305 (q) | J = 7.5 Hz | (C$\underline{H_2}$—CH$_3$)$_3$ |
| 3.08 (multiplet consisting of 8 peaks) | | (OC$\underline{H_2}$—CH$_3$)$_2$ |
| 4.27 (s) | $J_{HH}$ = 7.5 Hz $J_{POCH}$ = 9 Hz | (3) C—$\underline{H}$ |
| 4.94 (multiplet consisting of 8 peaks) | $J_{CH-CH}$ = 4.4 Hz, $J_{NHCH}$ = 6.8 Hz, $J_{PN-CH}$ = 12.5 Hz | (6) C—$\underline{H}$ |
| 5.53 (d) | $J_{CHCH}$ = 4.4 Hz | (5) C—$\underline{H}$ |

EXAMPLE 3

6-(4-methyl-1,3,2-dioxaphospholan-2-yl-amino) penicillanic acid, triethylammonium salt.

1.08 g (5 millimoles) of 6-aminopenicillanic acid are dissolved in 8 ml chloroform by the addition of 1.4 ml (10 millimoles) of triethylamine. The solution is cooled to —50° C and while stirring 0.54 ml (5 millimoles) of 4-methyl-2-chloro-1,3,2-dioxaphospholan dissolved in 2 ml chloroform are added under dry nitrogen. Stirring is continued for 15 minutes at —50° C and subsequently for 30 minutes at room temperature. 25 ml dry benzen are added. The triethylammoniumchloride formed is separated by filtration. During said filtration part of the product is lost, but the filtration is normally unnecessary when the product is to be used for further reactions.

The filtrate is concentrated in vacuum and is washed twice with dry ether which is removed by decanting. The remaining solvent is removed by evaporation over phosphorpentaoxide and 1.2 g of a solid white substance which is very hygroscopic is formed.

The IR spectrum (CDCl$_3$) shows characteristic bands at 1010 cm$^{-1}$ (P-O-C), 1610 cm$^{-1}$ (COO$^-$), and 1770 cm$^{-1}$ (-CO-, β-lactam).

The NMR spectrum (CDCl$_3$) shows characteristic signals at:

| δ ppm | | |
|---|---|---|
| 1.29 (t) | J = 7.5 Hz | (C$\underline{H_2}$CH$_3$)$_3$ |
| 1.6 (2 × s) | | (2) C(CH$_3$)(CH$_3$) |
| and partially hidden by the above mentioned signals | | CH$_3$—C$\underline{H}$(O—P)(C$\underline{H_2}$—O) |
| 3.04 (q) | J = 7.5 Hz | (C$\underline{H_2}$CH$_3$)$_3$ |
| 3.3–5.1 (3 × m) | | CH$_3$, $\underline{H}$, O, P, O, $\underline{H}$, $\underline{H}$ |
| 4.20 (s) | | (3) C—$\underline{H}$ |
| 4.4–5.0 (m) partially hidden by the above mentioned multiplets | | (6) C—$\underline{H}$ |
| 5.45 (d) | J = 4.5 Hz | (5) C—$\underline{H}$ |

EXAMPLE 4

6-(1,3,2-thiaoxaphospholan-2-yl-amino) penicillanic acid, triethylammonium salt.

1.08 g (5 millimoles) of 6-aminopenicillanic acid are dissolved in 8 ml dry acetonitrile by the addition of 1.40 ml (10 millimoles) of triethylamine while stirring. 0.48 ml (5 millimoles) of 2-chloro-1,3,2-thiaoxaphospholan in 2 ml dry acetonitrile are added dropwise under dry nitrogen and at a temperature of about —40° C. Subsequently the solution is stirred for about 1 hour at room temperature.

The precipitated triethylammoniumchloride is separated by filtration. (Part of the product is precipitated together with the salt. However, when the product formed is to be used for further reactions, it will normally be unnecessary to effect such a filtration).

30 ml dry ether are added to the filtrate, and the mixture is stirred for 30 minutes at 0° C before a precipate formed is separated by filtration. The product thus obtained is 1.1 g white hygroscopic 6-(1,3,2-thiaoxaphospholan-2-yl-amino)penicillanic acid, triethylammonium salt.

This product should be stored in vacuum over phosphorpentaoxide or in ampoules.

The IR spectrum (CHCl$_3$) shows characteristic bands at 1610 cm$^{-1}$ (COO$^-$) and 1770 cm$^{-1}$ (-CO-, β-lactam). The NMR spectrum shows characteristic signals at:

| δ ppm | | |
|---|---|---|
| 1.35 (t) | J 7.5 Hz | (C$\underline{H_2}$CH$_3$)$_3$ |
| 1.52 (s) | | (2) C(CH$_3$)(CH$_3$) |
| 2.35–about 3.0 (m) | partially hidden by the following signal | P—S—C$\underline{H_2}$— |
| 3.12 (q) | J ≃ 7.5 Hz | (C$\underline{H_2}$CH$_3$)$_3$ |
| 3.7–4.4 (m) | | P—O—C$\underline{H_2}$ |
| 4.24 (s) | | (3) C—$\underline{H}$ |
| 4.75–5.18 (multiplet consisting of 8 peaks) | $J_{CH-CH}$ ≃ 4.4 Hz, $J_{HNCH}$ ≃ 6.8 Hz, $J_{PN-CH}$ ≃ 14 Hz | (6) C—$\underline{H}$ |
| 5.54 (d) | $J_{CH-CH}$ ≃ 4.2 Hz | (5) C—$\underline{H}$ |

EXAMPLE 5

Diethylammonium salt of 6-ethylenephosphiteamidopenicillanic acid.

1.03 ml (10 millimoles) of diethylamine are added to 1.08 q (5 millimoles) of 6-aminopenicillanic acid suspended in 10 ml dry acetonitrile. After stirring in a nitrogen atmosphere for 2 minutes, a clear solution is obtained.

The NMR spectrum (CH$_3$CN) of a sample of the solution showed the following characteristic signals:

| δ ppm | | |
|---|---|---|
| 1.53 (s) | | (2) C(CH$_3$)(CH$_3$) |
| 1.59 (s) | | |

| δ ppm | | |
|---|---|---|
| 3.95 (s) | (3) | C—H |
| 4.49 (d) J_{HCCH} = 4.2 Hz | (6) | C—H~ 1 H |
| 5.37 (d) J_{HCCH} = 4.2 Hz | (5) | C—H~ 1 H |

The solution was cooled to −40° C and during a period of 5 minutes 0.45 ml (5 millimoles) of ethylene chlorophosphite dissolved in 2.5 ml dry acetonitrile was added. The cooling bath was then removed and the stirring continued in a nitrogen atmosphere for 0.5 hours, whereafter undissolved diethylammonium chloride was removed by filtration. The NMR spectrum (CH$_3$CN) of a sample of this solution showed the following characteristic signals:

| δ ppm | | |
|---|---|---|
| 1.53 (s) <br> 1.61 (s) | (2) | C<$\begin{matrix}CH_3\\CH_3\end{matrix}$ |
| 4.02 (s) | (3) | C—H |
| 3.7–4.5 (m) | | $\begin{matrix}H_2C-O\\H_2C-O\end{matrix}$>P— |
| 5.05 (multiplet consisting of 8 peaks) <br> J_{HCCH} = 4.3 Hz, J_{HNCH} = 6.4 Hz <br> J_{PNCH} = 11.8 Hz | (6) | C—H~ 1 H |
| 5.40 (d)   J_{HCCH} = 4.3 Hz | (5) | C—H~ 1 H |

This solution which contains diethylammonium salt of 6-ethylenephosphiteamidopenicillanic acid in an amount corresponding to 90–100% of the theoretical amount can be directly used for the synthesis of penicillins.

EXAMPLE 6

3-methyl-7β-(ethylenephosphiteamido)-ceph-3-em-4-carboxylic acid, diethylammonium salt.

4.28 g (20 millimoles) of 7β-amino-3-methyl-3-ceph-em-4-carboxylic acid are suspended in 10 ml pure chloroform and 4.16 ml (40 millimoles) of diethylamine. After a period of 15 minutes a clear solution is obtained. A further amount of 65 ml chloroform is added, and the solution is cooled to −40° C, whereafter 1.80 ml (20 millimoles) of ethylenechlorophosphite are added while stirring. Stirring is continued during a temperature raise to 0° C during 5 minutes and additionally for 15 minutes at 0° C. A sample of the solution is taken for NMR spectroscopy. The NMR spectrum shows a multiplet at 3.6–4.4 ppm corresponding to the four ethylenephosphiteamido protons, and a multiplet at 4.7–5.3 ppm corresponding to the two β-lactam protons. As a further proof of the configuration of the compound, the procedure described below is followed, and the same intermediate products as disclosed in examples 16 and 17 are formed. After addition of 2.53 ml (20 millimoles) of trimethylchlorosilane and stirring at room temperature for 30 minutes, NMR spectroscopy of the solution shows the same pattern as far as the ethylenephosphiteamido protons and the β-lactam protons are concerned as described in the above mentioned examples in connection with the trimethylsilyl ethylenephosphiteamido compound.

EXAMPLE 7

Trimethylsilyl 6-ethylenephosphiteamidopenicillanate.

To a suspension of 1.08 g (5 millimoles) of 6-APA in 12 ml of dry methylene chloride are added 1.4 ml (10 millimoles) of triethylamine, and the mixture is stirred at room temperature until a clear solution is formed. The solution is cooled to −40° C, and 0.45 ml (5 millimoles) of ethylenechlorophosphite dissolved in 3 ml of dry methylenechloride is added under dry nitrogen. The mixture is stirred for 15 minutes at −40° C, 15 minutes at 0° C and 15 minutes at room temperature, thereafter 0.67 ml (5.3 millimoles) of trimethylchlorosilane dissolved in 2 ml of methylenechloride is added. The mixture is stirred for 30 minutes at room temperature, and subsequently the precipitated triethylamine hydrochloride is filtered off. The solution is evaporated to form a hard, pale yellow oil.

The IR spectrum (CHCl$_3$) shows characteristic bands at 1780 cm$^{-1}$ (-CO-, β-lactam), 1720 cm$^{-1}$ (-CO-, ester) and 1010 cm$^{-1}$ (POC).

The NMR spectrum shows signals at:

| δ ppm | | |
|---|---|---|
| 0.30 (s) | | Si(CH$_3$)$_3$ |
| 1.53 (s) <br> 1.62 (s) | (2) | C<$\begin{matrix}CH_3\\CH_3\end{matrix}$ |
| 3.7–4.3 (m) | | $\begin{matrix}H_2C-O\\H_2C-O\end{matrix}$>P— |
| 4.30 (s) | (3) | C—H |
| 4.88 (multiplet consisting of 8 peaks) <br> J_{HCCH} = 4.5 Hz, J_{PNCH} = 12 Hz, <br> J_{HNCH} = 6.0 Hz | (6) | C—H |
| 5.46 (d)   J_{HCCH} = 4.5 Hz | (5) | C—H |

The NMR spectrum shows signals for dissolved triethylamine hydrochloride as well.

EXAMPLE 8

Trimethylsilyl 6-o-phenylenephosphiteamidopenicillanate 1 g of 6-APA is suspended in 15 ml of dry methylene chloride under nitrogen. To this mixture are added 1.42 ml of dry triethylamine and 0.62 ml of trimethylchlorosilane. After stirring for 1 hour the reaction mixture is cooled to −50° C, and a solution of 0.57 ml of o-phenylenechlorophosphite in 5 ml of dry methylene chloride is added dropwise. When the addition is complete the cooling is stopped, the mixture is stirred for 40 minutes, and the solvent is removed in vacuo. Dry benzene is added, and the triethylammoniumchloride formed is removed by filtration under nitrogen. The benzene is removed in vacuum to obtain 1.8 g (92%) of the desired product as an amorphous substance.

The IR spectrum (CHCl$_3$) shows characteristic bands at 1720 cm$^{-1}$ (-CO-, ester) and 1780 cm$^{-1}$ (-CO-, β-lactam).

NMR (DMSO-d$_6$) shows signals at:

| δ ppm | | |
|---|---|---|
| 0.1 (s) | | —Si(CH$_3$)$_3$ |
| 1.42 (s) <br> 1.56 (s) | } (2) | C$<^{CH_3}_{CH_3}$ |
| 4.14 (s) | | (3) C—H |
| 4.5 (m) | | (6) C—H |
| 4.89 (d) | J$_{5,6}$ ≃ 4 Hz | (5) C—H |
| 6.9 (m) | | o-phenylene |

The product of the synthesis described above is preferably used directly in the preparation of penicillins without any form of working up.

COMPARISON EXAMPLE (1,3,2-Dioxaphospholan)-2-yl-(6-ethylenephosphiteamido)-penicillanate.

4.07 g (10 millimoles) of 6-ethylenephosphiteamidopenicillanic acid, triethylammonium salt (prepared according to Example 1) are dissolved in 25 ml of dry acetonitrile, and 0.9 ml (10 millimoles) of ethylenechlorophosphite is added thereto at 0° C. The precipitated triethylammoniumchloride (1.2 g, 9 millimoles) is filtered off and the filtrate evaporated to a viscous oil. The IR spectrum (CHCl$_3$) shows characteristic bands at 3350 cm$^{-1}$ (NH), 1775 cm$^{-1}$ (-CO-, β-lactam), 1730 cm$^{-1}$ (-CO-, ester), and 1010 cm$^{-1}$ (POC).

The NMR spectrum (CDCl$_3$) shows signals at:

| δ ppm | | |
|---|---|---|
| 1.53 (s) <br> 1.62 (s) | } (2) | C$<^{CH_3}_{CH_3}$ |
| 3.7–4.3 (m) | | H$_2$C—O <br> H$_2$C—O $>$P— |
| 4.30 (s) | | (3) C—H |
| 4.88 (multiplet consisting of 8 peaks) | | |
| | J$_{HCCH}$ = 4.5 Hz, J$_{PNCH}$ = 12 Hz, <br> J$_{HNCH}$ = 6.0 Hz | (6) C—H |
| 5.45 (d) | J$_{HCCH}$ = 4.5 Hz | (5) C—H |

The spectrum shows signals for dissolved triethylamine hydrochloride as well.

The compound is very sensitive to hydrolysis and is only stable in an absolutely dry atmosphere.

EXAMPLE 9

Benzyl 6-ethylenephosphiteamidopenicillanate 5.10 g of benzyl 6-aminopenicillanate are dissolved in 45 ml of dry methylene chloride under nitrogen. 2.32 ml of triethylamine are added with cooling to −40° C, and a solution of 1.47 ml of ethylenechlorophosphite in 15 ml of dry methylene chloride is added dropwise. When this dropwise addition is complete, the cooling is removed, and the mixture is stirred for another 45 minutes and evaporated in vacuum. The residue is suspended in dry benzene and filtered (2.3 g of triethylammoniumchloride). The benzene solution is evaporated to form an amorphous, white substance (6.5 g, 98%).

The IR spectrum (CHCl$_3$) shows characteristic bands at 1745 cm$^{-1}$ (-CO-, ester) and 1780 cm$^{-1}$ (-CO-, β-lactam).

The NMR spectrum (CDCl$_3$) shows signals at:

| δ ppm | | |
|---|---|---|
| 1.41 (s) <br> 1.59 (s) | } (2) | C$<^{CH_3}_{CH_3}$ |
| 3.7–4.3 (m) | | CH$_2$—O <br> CH$_2$—O $>$P— |
| 4.40 (s) | | (3) C—H |
| 4.88 (multiplet consisting of 8 peaks) | | |
| | J$_{4,5}$ ≃ 4.3 Hz, J$_{PNCH}$ ≃ 12 Hz <br> J$_{HNCH}$ ≃ 5.6 Hz | (6) C—H |
| 5.14 (s) | | O—CH$_2$—φ |
| 5.45 (d) | J$_{5,6}$ = 4.3 Hz | (5) C—H |
| 7.31 (s) | | —φ |

EXAMPLE 10

Benzyl 6-diethylphosphiteamidopenicillanate 1 g of benzyl 6-aminopenicillanate is suspended in 20 ml of dry ether under nitrogen, and 0.47 ml of triethylamine is added. A solution of 0.5 ml of diethylchlorophosphite in 10 ml of dry ether is added dropwise with cooling to −40° C. Cooling is continued for 5 minutes after the addition is complete, and the reaction mixture is stirred for 40 minutes and filtered. Evaporation of the ether phase gives a white, amorphous substance (1.3 g, 94%).

The IR spectrum (CHCl$_3$) shows characteristic bands at 1740–1750 cm$^{-1}$ (-CO-, ester) and 1775–1785 cm$^{-1}$ (-CO-, β-lactam).

The NMR spectrum (CDCl$_3$) shows signals at:

| δ ppm | | |
|---|---|---|
| 1.38 (t) J 7.5 Hz | | CH$_3$—CH$_2$—O—P |
| 1.44 (s) <br> 1.62 (s) | } (2) | C$<^{CH_3}_{CH_3}$ |
| 4.18 (multiplet consisting of 8 peaks) <br> J$_{H,H}$ ≃ 7.5 Hz, J$_{POCH}$ ≃ 9 Hz*) | | CH$_3$—CH$_2$—O—P$<$ |
| 4.49 (s) | | (3) C—H |
| 5.05 (m) | | (6) C—H |
| 5.21 (s) | | CO—O—CH$_2$—φ |
| 5.59 (d) J$_{5,6}$ ≃ 4.5 Hz | | (5) C—H |

| | |
|---|---|
| 7.38 (s) | CO—O—CH$_2$—$\underline{\phi}$ |

\*)P—O—CH$\langle$ : $J_{PH}$ = 6.5–10 Hz

Jackmann and Sternhell. Application of Nucl. Magn. Res. in Org. Chem. 2nd Ed. 1969. p. 352.

EXAMPLE 11

Trichloroethyl 6-ethylenephosphiteamidopenicillanate 2.2 g (5.72 millimoles) of trichloroethyl 6-aminopenicillanate, hydrochloride suspended in 100 ml of ethyl acetate at 0° C are treated with 75 ml of ice-cold 2% aqueous sodium bicarbonate solution. The organic phase is further washed with 60 ml of ice-water containing 2 ml of 2% bicarbonate solution and subsequently dried over anhydrous MgSO$_4$. The solvent is evaporated in vacuum and the residue dissolved in 30 ml of dry methylene chloride. After cooling to −20° C under dry nitrogen 0.80 ml (5.72 millimoles) of triethylamine is added followed by dropwise addition of 0.515 ml (5.72 millimoles) of ethylene chlorophosphite dissolved in 6 ml of dry methylene chloride within 30 minutes. When the addition is complete the cooling bath is removed, and the mixture is stirred for 35 minutes at room temperature to complete the reaction. The solvent is evaporated in vacuum and the residue treated with 50 ml of benzene and triethylammonium chloride is removed by filtration under dry nitrogen. Lyophilization of the filtrate gives trichloroethyl 6-ethylenephosphiteamidopenicillanate in quantitative yield (2.5 g) as a white amorphous substance.

Analysis: Calculated for C$_{12}$H$_{16}$N$_2$O$_5$PSCl$_3$: N 6.4, S 7.3, Cl 24.3%, Found: N 6.1, S 7.7, Cl 24.4%.

The IR spectrum (CHCl$_3$) shows characteristic bands at 1760 cm$^{-1}$ (-CO-, ester) and 1775 cm$^{-1}$ (-CO-, β-lactam).

The NMR spectrum (CDCl$_3$) shows characteristic signals at:

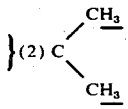

| δ ppm | | |
|---|---|---|
| 1.58 (s) | | (2) C(CH$_3$)(CH$_3$) |
| 1.72 (s) | | |
| 3.7–4.5 (m) | | CH$_2$—O, CH$_2$—O, P— |
| 4.53 (s) | | (3) C—$\underline{H}$ |
| 4.75–5.15 (m) 3H | The middle peaks in the AB system resulting from —OCH$_2$CCl$_3$ occur at 4.77 and 4.79 ppm, 6 of the peaks of the (6) C—$\underline{H}$ octet escapes the methylene group, and the following approximate values are concluded for (6) C—$\underline{H}$: | |
| | δ = 4.95 ppm, J$_{5,6}$ ≈ 4.4 Hz, | |
| | J$_{HNCH}$ ≈ 6.2 Hz and | |
| | J$_{PNCH}$ ≈ 12 Hz | |

| | | |
|---|---|---|
| 5.57 (d) | J$_{5,6}$ ≈ 4.4 Hz (5) C—$\underline{H}$ | |

EXAMPLE 12

2',2',2'-trichloroethyl-3-methyl-7β-(ethylenephosphiteamido)-ceph-3-em-4-carboxylate To a suspension of 2.07 g (4 millimoles) of 2',2',2'-trichloroethyl-3-methyl-7β-amino-ceph-3-em-4-carboxylate p-toluenesulfonic acid salt in methylene chloride is added a semi-saturated sodium hydrogen carbonate solution. After shaking the organic phase is separated and the water phase is extracted once more with methylene chloride. The combined organic phases are dried (MgSO$_4$) and evaporated to dryness under vacuum. The residue is dissolved in 10 ml of dry acetonitrile, and 0.57 ml (4 millimoles) of triethylamine is added. The mixture is cooled to about −30° C on a cooling bath, and 0.36 ml (4 millimoles) of ethylene chlorophosphite is added with stirring. The temperature is raised to room temperature within a few minutes, and stirring is continued at this temperature for 20 minutes. Precipitated triethylammonium chloride is filtered off, and a sample of the filtrate is subjected to NMR spectroscopy. The NMR spectrum shows a multiplet at 3.7–4.4 ppm corresponding to the four ethylene phosphiteamido protons and a multiplet at 4.4–5.3 ppm corresponding to the β-lactam protons and the methylene protons in the trichloroethyl ester.

Evaporation in vacuum gives an oily residue of 2',2',2'-trichloroethyl-3-methyl-7β-(ethylenephosphiteamido)-ceph-3-em-4-carboxylate.

The IR spectrum (CHCl$_3$) shows characteristic bands at 1740 cm$^{-1}$ (-CO-, ester) and 1780 cm$^{-1}$ (-CO-, β-lactam).

The NMR spectrum (CDCl$_3$) shows the above mentioned four ethylene phosphiteamido protons and the β-lactam and methylene protons in the trichloroethyl ester and, besides, signals at:

| δ ppm | | |
|---|---|---|
| 3.3–3.6 | (2) —CH$_2$— | |
| 2.2 (s) | (3) —CH$_3$— | |

EXAMPLE 13 p-Bromophenacyl 6-ethylenephosphiteamidopenicillanate 1.94 g (4.7 millimoles) of p-bromophenacyl-6-aminopenicillanate, liberated from the hydrochloride in a similar way as in Example 11 are dissolved in 20 ml of dry methylene chloride. The solution is cooled to −20° C under dry nitrogen, and 0.66 ml (4.7 millimoles) of triethylamine is added thereto. During 30 minutes 0.424 ml (4.7 millimoles) of ethylenechlorophosphite dissolved in 5 ml of dry methylene chloride is added, whereupon the temperature is raised to room temperature with stirring for further 30 minutes. After evaporation in vacuum the residue is treated with 30 ml of benzene, the triethylammonium chloride is removed by filtration under dry nitrogen, and the desired p- bromophenacyl 6-ethylenephosphiteamidopenicillanate is recovered by lyophilization of the filtrate in a yield of 98% as a white, amorphous substance.

Analysis: Calculated for $C_{18}H_{20}N_2O_6PSBr$: N 5.6, S 6.4, Br 15.9%, Found: N 5.1, S 6.2, Br 15.7%.

The IR spectrum ($CHCl_3$) shows strong absorptions at 1755 cm$^{-1}$ (-CO-, ester) and 1775 cm$^{-1}$ (-CO-, β-lactam).

The NMR spectrum shows characteristic signals at:

| δ ppm | | |
|---|---|---|
| 1.68 (s) <br> 1.72 (s) | } (2) C$\diagup$CH$_3$ $\diagdown$CH$_3$ | |
| 3.6–4.5 (m) | CH$_2$—O <br> \|      $\diagdown$P— <br> CH$_2$—O $\diagup$ | |
| 4.47 (s) | | (3) C—H |
| 4.90 (m) | | (6) C—H |

From the multiplet (8 peaks) the following can be concluded:
$J_{5,6} \simeq 4.4$ Hz
$J_{HXCH} \simeq 5.9$ Hz
$J_{PXCH} \simeq 12$ Hz

| 5.35 (m) | | —O—CH$_2$—CO—φBr |
|---|---|---|
| 5.50 (d) | $J_{5,6} \simeq 4.4$ Hz | (5) C—H |
| 7.66 (m) | | —C$_6$H$_4$—Br |

EXAMPLE 14

Pivaloyloxymethyl 6-ethylenephosphiteamidopenicillanate

A solution of 10.4 g of pivaloyloxymethyl 6-aminopenicillanate, p-toluenesulfonate in 150 ml of methylene chloride is shaken with 375 ml of ice-cold 2% bicarbonate solution. Then the solution is shaken with 300 ml of ice-water, to which 10 ml of 2% bicarbonate has been added in advance. The dried organic phase is cooled to −10° C under nitrogen. 2 g of triethylamine are added followed by slow dropwise addition of 2.52 g of ethylenechlorophosphite dissolved in 20 ml of methylene chloride. When the addition is complete, the temperature is raised to room temperature, and stirring is continued for 30 minutes. The reaction mixture is evaporated to dryness in vacuum and re-dissolved in 100 ml of dry benzene. The triethylammonium chloride formed is filtered off, and the solution is re-evaporated in vacuum to give 8.0 g (90%) of an amorphous substance.

The IR spectrum ($CHCl_3$) shows characteristic bands at 1765 cm$^{-1}$ (-CO-, ester) and 1775 cm$^{-1}$ (-CO-, β-lactam).

The NMR spectrum ($CDCl_3$) shows signals at:

| δ ppm | |
|---|---|
| 1.18 (s) | C(CH$_3$)$_3$ |
| 1.51 (s) <br> 1.63 (s) | } (2) C$\diagup$CH$_3$ $\diagdown$CH$_3$ |
| 3.6–4.3 (m) | H$_2$C—O <br> \|      $\diagdown$P— <br> H$_2$C—O $\diagup$ |
| 4.39 (s) | (3) C—H |
| 4.89 (multiplet consisting of 8 peaks) <br> $J_{5,6} \simeq 4.5$ Hz   $J_{PXCH} \simeq 12$ Hz <br> $J_{HX,H} \simeq 6.0$ Hz | (6) C—H |
| 5.45 (d)    $J_{5,6} \simeq 4.5$ Hz | (5) C—H |
| 5.79 (m) | —O—CH$_2$—O— |

EXAMPLE 15

7β-Phenoxyacetamido-3-methyl-3-cephem-4-carboxylic acid.

4.28 g (20 millimoles) of 7β-amino-3-methyl-3-cephem-4-carboxylic acid are suspended in 50 ml of dry acetonitrile, 5.76 ml (40 millimoles) of triethylamine are added thereto and the mixture is cooled to −40° C. Then 1.80 ml (20 millimoles) of ethylene chlorophosphite are added and the temperature is raised by means of an ice-bath to 0°–5° C. The mixture is stirred on ice-bath for 30 minutes. The temperature is again lowered to −40° C and 2.53 ml (20 millimoles) of trimethylchlorosilane is added. During 30 minutes the temperature is raised to room temperature, at which temperature the mixture is stirred for 20 minutes. The mixture is then cooled to −20° C and 3.41 g (20 millimoles) of phenoxyacetyl chloride is added. The mixture is stirred at −10° C for 30 minutes and for 1 hour at 5° C. The reaction mixture is cooled to −10° C, and 50 ml of acetonitrile/water (1:1) is added thereto. The mixture is stirred on an ice-bath for 30 minutes and then extracted three times with methylene chloride. The combined organic phases are washed once with water, dried over $Na_2SO_4$ and evaporated in vacuum to amorphous powder.

Yield: 6.8 g (97%).

The IR spectrum (KBr) shows characteristic bands at 1685–1775 cm$^{-1}$ (amide, acid and β-lactam-CO-).

The NMR spectrum (DMSO-d$_6$) shows characteristic signals at:

| δ ppm | |
|---|---|
| 2.08 (s) | (3) —CH$_3$ |
| 3.2–3.9 (2d) | (2) —CH$_2$— |
| 4.68 (s) | —O—CH$_2$—C=O |
| 5.12 (d) | (6) CH |
| 5.68 (q) | (7) CH |
| 6.8–7.55 (m) | Aromatic H |

EXAMPLE 16

7β-(D(−)-α-phenylglycylamido)-3-methyl-ceph-3-em-4-carboxylic acid (Cephalexin).

8.56 g (40 millimoles) of 7β-amino-3-methyl-3-cephem-4-carboxylic acid are suspended in 200 ml of dry methylen chloride. 11.3 ml (80 millimoles) of triethylamine are added and the mixture is cooled to 0° C. Subsequently 5.06 ml (40 millimoles) of trimethylchlorosilane are added while stirring. The temperature is raised to room temperature over a period of 30 minutes, and the mixture is stirred for further 30 minutes. After cooling to −40° C 3.60 ml (40 millimoles) of ethylene chlorophosphite are added. During a period of 15 minutes the temperature is raised to −10° C, and the stirring is continued for 30 minutes at said temperature. A sample for NMR spectroscopy was taken. The methylene in said sample is replaced by chloroform. The NMR spectrum of the chloroform containing sample showed a multiplet at 3.6–4.3 ppm corresponding to the four ethylenephosphiteamido protons and a multiplet at 4.7–5.3 ppm corresponding to the β-lactam protons and a singlet at 0.3 ppm corresponding to the trimethylsilylester protons.

10.72 g (52 millimoles) of D-(−)-β-phenylglycylchloride, HCl are then added to the reaction mixture, and said mixture is stirred for 5 hours at −10° C. Subsequently 200 ml water and some ice are added and the mixture is stirred for 30 minutes at 3°–5° C. The pH is adjusted at 7.0 with 30% sodium hydroxide solution and the reaction mixture is filtered through Celite which is thoroughly washed with water. The organic phase is separated and the aqueous phase is washed twice with 50 ml methylene chloride. The volume of the aqueous phase is reduced to 240 ml under vacuum and pH adjusted to 5.7 with 6N hydrochloric acid. 11.53 g (80 millimoles) of β-naphthol dissolved in 20 ml ethanol are added during a period of 2 hours while stirring. Stirring is continued for about 2 hours while lowering the temperature to 5° C. Finally the reaction mixture is left to stand overnight at 5° C. The precipitated cephalexin-β-naphthol complex is separated by filtration and washed with water and butylacetate. The washed precipitate is suspended in 160 ml water and 160 ml butylacetate and the pH is adjusted at 1.5 with a 2N sulfuric acid solution. Subsequently the mixture is filtered and the aqueous phase is washed twice with 80 ml butylacetate. The pH-value of the aqueous phase is adjusted at 4.5 with triethylamine and the volume of the mixture is reduced under vacuum to 90 ml. 100 ml of 1,2-dimethoxyethane are added and the mixture is stirred while being cooled to 5° C over a period of about 2 hours. The mixture is left to stand overnight in a refrigerator at 5° C. The precipitate formed is separated by filtration, washed with water and dried in an exicator.

Yield: 7.0 g pure cephalexin having an IR spectrum (KBr) showing characteristic bands at 1500–1610 cm$^{-1}$ (-COO$^-$), 1690 cm$^{-1}$ (-CO-, amide) and 1765 cm$^{-1}$ (-CO-, β-lactam) and a NMR spectrum (D$_2$O-NaHCO$_3$) with the following signals:

| δ ppm | | |
|---|---|---|
| 1.90 (s) | | (3) —CH$_3$ |
| 3.03 and 3.40 (2d) | J = 18 Hz | (2) —CH$_2$— |
| 4.93 (d) | J = 5 Hz | (6) CH |
| 5.20 (s) | | α-CH |
| 5.60 (d) | J = 5 Hz | (7) CH |
| 7.44 (s) | | Aromatic H | which correspond exactly to an authentic sample of cephalexin.

EXAMPLE 17

7β-(D(−)-α-phenylglycylamido)-3-methyl-ceph-3-em-4-carboxylic acid (Cephalexin)

4.28 g (20 millimoles) of 7β-amino-3-methyl-3-cephem-4-carboxylic acid are suspended in 50 ml of dry acetonitrile, 5.76 ml (40 millimoles) of triethylamine are added and the mixture is cooled to −40° C. Then 1.80 ml (20 millimoles) of ethylene chlorophosphite are added and the temperature is raised by means of an ice-bath to 0°–5° C. The mixture is stirred on an ice-bath for 30 minutes. The temperature is again lowered to −40° C and 2.53 ml (20 millimoles) of trimethylchlorosilane is added. During 30 minutes the temperature is raised to room temperature, at which temperature the mixture is stirred for 20 minutes. The precipitated triethylammonium chloride is filtered off (4.65 g), and from the filtrate a sample is taken for NMR spectroscopy. The spectrum shows a multiplet at 3.6–4.3 ppm corresponding to the four ethylene phosphiteamido protons and a multiplet at 4.7–5.3 ppm corresponding to the β-lactam protons and the trimethylsilylester protons at 0.3 ppm. The reaction mixture is cooled to 0° C and 4.33 g (21 millimoles) of D(−)-α-phenylglycylchloride, hydrochloride are added while stirring. During 30 minutes the temperature is raised to room temperature, at which temperature the mixture is stirred for 2 hours. The mixture is cooled on an ice-bath and 40 ml of ice-water are added. The mixture is stirred on the ice-bath for 30 minutes. The pH is now adjusted to 4.5 with triethylamine and stirring is continued overnight and finally at a temperature of about 0° C. The precipitated cephalexin is filtered off and washed with a small amount of 50% aqueous acetonitrile.

Yield: 6.3 g (90%), which after purification in a manner known per se gives the pure cephalexin with an IR spectrum and a NMR spectrum identical with those described in Example 16.

EXAMPLE 18

2′,2′,2′-trichloroethyl-7β-(D(−)-α-phenylglycylamido)-3-methyl-3-cephem-4-carboxylate.

A solution of 4 millimoles of 2′,2′,2′-trichloroethyl-3-methyl-7β-(ethylenephosphiteamido)-ceph-3-em-4-carboxylate in 7 ml of deuteroform is prepared as described in Example 12 without removing the formed triethylammonium chloride. A $^{31}$P NMR spectrum of the solution shows a band at −133.4 ppm (85% H$_3$PO as external standard) for ethylenephosphiteamido. 0.828 g (4 millimoles) D(−)-α-phenylglycylchloride, hydrochloride is now added, and the mixture is stirred at room temperature for 1 hour. A new $^{31}$P NMR spectrum of the turbid solution shows a band at −167.6 ppm, which corresponds exactly with the authentic ethylenechlorophosphite, and the band of the ethylenephosphiteamido has completely disappeared.

High voltage electrophoresis at a pH of 2 shows the formation of one new plet.

The mixture is worked up by the addition of water and extracted three times with methylene chloride. The combined organic phases are dried over MgSO$_4$ and evaporated to dryness. The product obtained is 2′,2′,-2′-trichloroethyl-7-(D(−)-α-phenylglycylamido)-3-methyl-3-cephem-4-carboxylate as a salt.

Yield: 1.6 g.

The IR spectrum (KBr) of the substance in the form of the free amine shows characteristic bands at 1680 cm$^{-1}$ (amide, -CO), 1740–1780 cm$^{-1}$ (ester and $\beta$-lactam-CO-).

The NMR spectrum (DMSO-d$_6$) of the product in the form of the free amine shows characteristic signals at:

| δ ppm | | |
|---|---|---|
| 2.1 (s) | | (3) —CH$_3$ |
| 3.52 (s) | | (2) —CH$_2$— |
| 4.9–5.4 (m) | ester —CH$_2$—, | (6) —CH, α-CH |
| 5.5–6.0 (m) | | (7) —CH |
| 7.2–7.8 (m) | | Aromatic H |

From the aqueous phase further 0.3 g of 2′,2′,2′-trichloroethyl-7-(D(−)-α-phenylglycylamido)-3-methyl-3-cephem-4-carboxylate is obtained.

EXAMPLE 19

Ampicillin

Method A

4.33 g (21 millimoles) of D(−)-phenylglycylchloride, hydrochloride are added in portions over a period of 1 minute to a solution in methylene chloride of 20 millimoles of trimethylsilyl-6-(ethylenephosphiteamido)-penicillanate prepared as described in Example 7 and without removing triethylammoniumchloride, at a temperature of 0° C. The progress of the reaction is followed by penicillinase titration which after a period of 2 hours at 0° C shows that a yield of above 70% has been obtained. At this time the reaction mixture is poured into 100 ml ice-water, and after stirring for 15 minutes the reaction mixture is filtered. The water phase is covered by 20 ml ethylacetate and the pH-value of the water phase is adjusted at 2 with a NaOH solution. Subsequently, the ampicillin formed is precipitated as a sparingly soluble salt with $\beta$-naphthalenesulphonic acid while maintaining the pH-value at 2. The reaction mixture is left to stand for 12 hours at 4° C and is subsequently filtered and the residue is washed with 0.01 N HCl and ethylacetate. After drying in vacuum 7.2 g white ampicillin $\beta$-naphthalenesulphonic acid salt corresponding to 64.5% of the theoretical amount are obtained. A high-voltage electrophogram showed one spot with mobility identical to that of authentic ampicillin. The IR spectrum was identical to that of the $\beta$-naphthalenesulphonic acid salt of authentic ampicillin.

Method B

5 millimoles of 6-(1,3,2-thiaoxaphospholan-2-yl-amino)-penicillanic acid trialkylammonium salt dissolved in 10 ml deuteriochlororform are prepared as described in Example 4 with the exception that deuteriochloroform is used instead of acetonitrile. 0.67 ml (5 millimoles) of trimethylchlorosilan is added dropwise under nitrogen. After stirring at room temperature for 1 hour 0.5 ml is taken for NMR spectroscopy. (The sample is reintroduced into the reaction mixture after the completion of the analysis.)

The NMR spectrum shows the following characteristic signals relative to the trimethylsilylester:

| δ ppm | | |
|---|---|---|
| 1.10 (t) | J ≃ 7.5 Hz | N(CH$_2$CH$_3$)$_3$, HCl |
| About 1.25 (s) partially hidden by the above mentioned signal | | |
| 1.33 (s) | | }(2) C$\begin{smallmatrix}/CH_3\\ \backslash CH_3\end{smallmatrix}$ |
| 2.0–2.7 (m) partially hidden by the following signal | | P—S—CH$_2$— |
| 2.87 (m~2 × q) | J$_{CHCH}$ ≃ 7.5 Hz | |
| | J$_{CHN^+H}$ ≃ 5.2 Hz | N(CH$_2$CH$_3$)$_3$, HCl |
| 3.4–4.2 (m) | | P—O—CH$_2$— |
| 4.0 (s) | | (3) C—H |
| 4.55–5.0 (multiplet consisting of 8 peaks) | | |
| | J$_{HCCH}$ ≃ 4.2 Hz | J$_{HCNH}$ ≃ 7.0 Hz |
| | J$_{PNCH}$ ≃ 14 Hz | (6) C—H |
| 5.16 (d) | J ≃ 4.2 Hz | (5) C—H |
| 11.1 (wide band) | | N(CH$_2$CH$_3$)$_3$, HCl |

5 millimoles of D(−)-phenylglycylchloride, hydrochloride are added to the above mentioned reaction mixture at 0° C.

Penicillinase titration of the reaction mixture after a reaction time of 50 minutes at 0° C shows that a yield of 65% has been obtained.

The identity of the product was proved by high voltage electrophoresis of a hydrolysed sample of the reaction mixture.

The reaction product can be recovered by methods which are well known per se.

EXAMPLE 20 p-Hydroxyampicillin.

2.16 g (10 millimoles) of 6-aminopenicillanic acid are dissolved in 8 ml dry alcohol-free chloroform by the addition of 2.8 ml (40 millimoles) of triethylamine, 1.36 ml (10 millimoles) of trimethylchlorosilan are added dropwise and the reaction mixture is stirred for 1 hour at room temperature. At −50° C 0.9 ml (10 millimoles) of ethylene chlorophosphite dissolved in 2 ml dry alcohol-free chloroform are added dropwise. The reaction mixture is stirred for 1 hour at 0° C.

While stirring and at a temperature of 0° C the reaction mixture is added to a slurry containing D(−)-p-hydroxy-phenylglycylchloride, hydrochloride in 5 ml chloroform. The acidchloride was prepared from 1.67 g (10 millimoles) of D(−)-p-hydroxy-phenylglycin by chlorination with phosphorpentachloride in acetylchloride and with dimethylformamide as catalyst.

After a reaction period of 7 minutes penicillinase titration of the reaction mixture shows a conversion corresponding to 21% penicillin. After a period of 35 minutes the yield obtained is 42%. If the phosphiteamido compound is added to a portion of the acidchloride prepared from 20 millimoles of the acid, the yield is increased to about 70%.

The P$^{31}$ NMR spectroscopy of the reaction mixture shows the ethylenechlorophosphite is formed by the reaction between the phosphiteamido compound and D(−)-p-hydroxy-phenylglycylchloride. p-Hydroxypenicillin can be recovered from the reaction mixture by well known methods, so as to obtain a white, crystalline product having the following spectroscopic properties:

The IR spectrum (KBr) shows characteristic bands at 1510 cm$^{-1}$ (amide II), 1600 cm$^{-1}$ (COO-), 1680 cm$^{-1}$ (amide I) and 1770 cm$^{-1}$ (-CO-, $\beta$-lactam).

The NMR spectrum (DMSO-d$_6$-D$_2$O) shows characteristic signals at:

| δ ppm | | |
|---|---|---|
| 1.4 (s) | | }(2) CH$_3$ / \ CH$_3$ |
| 1.5 (s) | | |
| 4.2 (s) | | (3) C—H |
| 5.0 (s) | | $\phi$—CH— |
| 5.4 (d) | J ≃ 4.5 Hz | (6) C—H |
| 5.5 (d) | J ≃ 4.5 Hz | (5) C—H |
| 6.8 | J ≃ 9 Hz | }—$\phi$— |
| 7.3 | J ≃ 9 Hz | |

EXAMPLE 21 p-Hydroxyampicillin.

Method A

0.97 g of D(—)-p-hydroxy-N-carboxyphenylglycylanhydride (5 millimoles) is suspended in 5 ml of dry methylene chloride, and a solution of 0.41 ml of pyridine (5 millimoles) and 0.45 ml of ethylenechlorophosphite in 5 ml of dry methylene chloride are added dropwise. The clear solution formed is slowly added to a solution of 5 millimoles of trimethylsilyl-6-ethylenephosphiteamidopenicillanate (prepared as described in Example 7) in 15 ml of dry methylene chloride, and the reaction is followed titrimetrically:

| Time | Yield |
|---|---|
| 0.5 h | 25% |
| 1.5 h | 40% |
| 16 h | 56% |

The solution is diluted to 100 ml with dry methylene chloride and 0.04 ml water and 0.09 g toluenesulphonic acid is added. This causes the penicillin formed to be precipitated as a white powder which is removed by filtration. The yield is 1.83 g. After dissolving in methanol and reprecipitation with ether the substance shows only one spot on high voltage paper electrophoresis at pH 7 which is identical to that of authentic p-hydroxyampicillin.

In a IR spectrum (KBr) the substance shows characteristic bands at 1770 cm$^{-1}$, 1680 cm$^{-1}$, 1600 cm$^{-1}$ and 1510 cm$^{-1}$.

The NMR spectrum (DMSO-D$_2$O, Ext. std. TMS) shows characteristic signals at:

| δ ppm | | |
|---|---|---|
| 1.4 (s) | | }(2) C / CH$_3$ \ CH$_3$ |
| 1.5 (s) | | |
| 4.2 (s) | | (3) C—H |
| 5.0 (s) | | Benzyl C—H |
| 5.4 (d) | J$_{HCCH}$ = 4.5 Hz | }(5,6) C—H |
| 5.5 (d) | J$_{HCCH}$ = 4.5 Hz | |
| 6.8 (d) | J$_{HCCH}$ = 9 Hz | }Aromatic C—H |
| 7.3 (d) | J$_{HCCH}$ = 9 Hz | |

To obtain a crystalline material, the product may be processed according to generally known methods. Thus, the product may be dissolved in water at a low pH, so as to obtain a solution which is filtered and concentrated to a small volume. Finally, the product is precipitated at the isoelectric point.

Method B

12.55 g of D(—)-p-hydroxy-phenylglycin are suspended in 150 ml of dry methylene chloride and 30 ml of trimethylchlorosilane are added. The mixture is heated to a temperature at which reflux starts, and 31,5 of triethylamine are added dropwise. When the addition is completed, 150 ml of dry benzene are added and the mixture is refluxed for 1 hour and cooled to room temperature. The precipitated triethylamine hydrochloride (32 g) is removed by filtration. The filtrate is slowly added to a refluxing solution of 15 g of phosgene in 150 ml of methylene chloride and 150 ml of benzene and the mixture is refluxed overnight. The clear, slightly yellow solution is concentrated in vacuum to about 100 ml, whereby D(—)-p-trimethylsilyloxy-N-carboxyphenylglycylanhydride separates as tiny needles which melt with destruction at 240° – 255° C. The yield of the pure compound is 13.3 g, and another crop of crystals may be obtained from the filtrate upon addition of hexane.

Analysis: Calculated for C$_{12}$H$_{15}$NO$_4$Si: C:54.32, H:5.71, N:5.28%, Found: C:54.29, H:5.71, N:5.30%.

The IR spectrum (KBr) shows characteristic absorption at 1780 cm$^{-1}$, 1800 cm$^{-1}$, 1850 cm$^{-1}$ and 1870 cm$^{-1}$ (anhydride), 840 cm$^{-1}$ (trimethylsilyl).

The NMR spectrum (CDCl$_3$, Ext. std. TMS) shows characteristic signals at:

| δ ppm | | |
|---|---|---|
| 0.25 (s) | | Trimethylsilyl |
| 5.25 (s) | | Benzyl C—H |
| 6.4 (d) | J$_{HCCH}$ = 9 Hz | }Aromatic C—H |
| 7.2 (d) | J$_{HCCH}$ = 9 Hz | |
| 6.5–7.3 broad band | | N—H |

1.23 g of this compound (5 millimoles) and 0.56 g of pyridine hydrochloride are dissolved in 12.5 ml of dry methylene chloride and heated to reflux. A solution of 5 millimoles of trimethylsilyl 6-ethylenephosphiteamidopenicillanate in 12.5 ml of dry methylene chloride is added during 45 minutes. Enzymatic titration 10 minutes after the addition is completed shows a penicillin yield of 39%, while titration after one and two hours both shows 50% yield.

IR spectroscopy and thin layer chromatography (silicagel, acetone:benzene - ratio 1:1) shows the presence of unreacted anhydride, and addition of another 5 millimoles of trimethylsilyl-6-phosphiteamidopenicillanate raises the titrimetric yield to 73%. No evolution of gas or precipitation of polymeric material was observed during the reaction.

Identification of the penicillin formed in the reaction is made by comparison with authentic p-hydroxyampicillin in high voltage electrophoresis at pH 7.

Precipitation of the crude penicillin and the subsequent purification may be performed as described in method A.

EXAMPLE 22

Pivaloyloxymethyl 6-phenoxyacetamidopenicillanate.

3.3 g of pivaloyloxymethyl 6-aminopenicillanate are dissolved in 15.0 ml of dry toluene. 1.4 ml of triethylamine are added and the solution is cooled to about −40° C. Under dry nitrogen and while stirring a solution of 0.9 ml of ethylene chlorophosphite in 5.0 ml of dry toluene, also cooled to about −40° C is added. After the addition stirring is continued for about 30 minutes, whereby the temperature raises to room temperature. Triethylammoniumchloride formed is filtered off, and a solution of the trimethylsilylester of phenoxyacetic acid prepared in the following manner is added. 1.5 g of phenoxyacetic acid is dissolved in 20.0 ml of dry toluene by the addition of 1.4 ml of triethylamine. 1.3 ml of trimethylchlorosilane is added, and after cooling to room temperature the triethylammoniumchloride obtained is separated by filtration.

The combined toluene solutions are refluxed for 20 hours, cooled to room temperature and washed twice with a 2% cold NaHCO$_3$-solution and twice with water, dried over Na$_2$SO$_4$ and evaporated in vacuum to dryness. The residue is stirred with petrolether, whereupon the substance formed is filtered off. In this manner there is obtained 2.3 g of a substance having an IR spectrum (CHCl$_3$) showing characteristic bands at 1505 cm$^{-1}$ (amide II), 1685 cm$^{-1}$ (amide I), 1750 cm$^{-1}$ (-CO-, ester) and 1785 cm$^{-1}$ (-CO-, β-lactam) and a NMR spectrum (CDCl$_3$) showing signals at:

| δ ppm | | |
|---|---|---|
| 1.20 (s) | | C(CH$_3$)$_3$ |
| 1.52 (s) | | |
| 1.60 (s) | | }(2) C<CH$_3$ / CH$_3$ |
| 4.47 (s) | | (3) C—H |
| 4.54 (s) | | φ—O—CH$_2$—CO—NH |
| 5.4–6.0 (m) | J$_{5,6}$ ≃ 4.0 Hz | { (5) C—H / (6) C—H / —O—CH$_2$—O— |
| 6.8–7.5 (m) | | φ—O—CH$_2$ |

EXAMPLE 23

2′,2′,2′-trichloroethyl-3-methyl-7β-(N-(tert.-butoxycarbonyl)-D(−)-α-phenylglycylamido)-ceph-3-em-4-carboxylate.

4 millimoles of N-(tert.-butoxycarbonyl)-D(−)-α-phenylglycine trimethylsilylester prepared from 1.01 g (4 millimoles) of N-(tert.-butoxycarbonyl)-D(−)-α-phenylglycine, 15 ml of chloroform, 0.57 ml (4 millimoles) of triethylamine and 0.51 ml (4 millimoles) of trimethylchlorosilane by stirring for 30 minutes are added to a solution of 4 millimoles of 2′,2′,2′-trichloroethyl-3-methyl-7β-(ethylenephosphiteamido)-ceph-3-em-4-carboxylate in 15 ml of pure chloroform prepared as described in Example 12, except for the filtration to remove triethylammonium chloride. 40 ml of toluene are added, the chloroform is evaporated, and the mixture is refluxed (110° C) for 18 hours. Then the mixture is evaporated in vacuum to dryness. The residue is dissolved in methylene chloride and washed twice with diluted hydrochloric acid and twice with a solution of sodium hydrogen hydrochloric acid and twice with a solution of sodium hydrogen carbonate. The solution is dried over Na$_2$SO$_4$ and evaporated in vacuum to form an amorphous powder. Yield: 2.0 g (86%) of 2′,2′,2′-trichloroethyl-3-methyl-7β-(N-(tert.-butoxycarbonyl)-D(−)-α-phenylglycylamido)-ceph-3-em-4-carboxylate.

The IR spectrum (KBr) shows characteristic bands at 1680–1740 cm$^{-1}$ (broad, -CO-, ester and amide) and 1782 cm$^{-1}$ (-CO-, β-lactam).

The NMR spectrum (CDCl$_3$) shows characteristic signals at:

| δ ppm | | |
|---|---|---|
| 1.40 (s) | | —C(CH$_3$)$_3$ |
| 2.17 (s) | | (3) —CH$_3$ |
| 2.9–3.65 (2d) | J = 18 Hz | (2) —CH$_2$— |
| 4.6–5.1 (m) | | —O—CH$_2$—CCl$_3$ and (6) C—H |
| 5.25 (d) | | α—C—H |
| 5.8 (m) | | { (7) C—H and amide N—H |
| 7.0 (d) | | amide N—H |
| 7.38 (s) | | φ— |

EXAMPLE 24

Phenoxymethylpenicillin

Method A

To a solution of 10 millimoles of trimethylsilyl-(6-ethylenephosphiteamido)-penicillanate (prepared as described in Example 7, from 2.16 g of 6-APA) in dry methylene chloride are added 1.51 g (10 millimoles) of phenoxyacetic acid, and the mixture is stirred at room temperature with dry air bubbling through. After a reaction period of 6 hours at room temperature the reaction mixture shows a penicillin yield of 82% by enzymatic titration. The reaction mixture is cooled to 0° C, and 5 ml of pyridine are added followed by 25 ml of dimethylsulfoxide, whereafter the reaction mixture is poured into 500 ml of ice-cold 10% NaCl solution and stirred for 30 minutes. Then 150 ml of ethylacetate are added and the pH adjusted to 2. After 30 minutes the phases are separated, and the water phase is extracted three times with ethylacetate. 25 ml of water are added to the combined organic phases, and the pH is adjusted to 7 with KOH. The water phase is separated, 150 ml of n-butanol added and the water removed by azeotropic vacuum destillation. The crystalline crude product thus precipitated is filtered off. Yield: 3.16 g (81%) of a purity of 76% determined by penicillinase titration. The white, crystalline product shows a characteristic absorption in the IR spectrum corresponding to that of the potassium salt of phenoxymethylpenicillin, and the NMR spectrum also shows signals which are characteristic of said compound.

A further 10% yield can be obtained from the organic phases, and further purification of the crude product may be effected by well known methods.

Method B 0.65 g of phenoxyacetic acid is added to a reaction mixture resulting from a synthesis as described in Example 8 (1.8 g of trimethylsilyl 6-o-phenylenephosphiteamidopenicillanate) while cooling to 0° C. After 30 minutes the cooling is removed, and the mixture is stirred for 3 hours at room temperature. Penicillase titration of the reaction mixture shows a 60% yield of phenoxymethylpenicillin which is isolated as the potassium salt after hydrolysis with diethylamine and 25% magnesium chloride solution.

EXAMPLE 25

Pivaloyloxymethyl 6-phenoxyacetamidopenicillanate 1.08 g of pivaloyloxymethyl 6-aminopenicillanate are dissolved in 20 ml of dry ethylacetate under nitrogen, and 0.46 ml of triethylamine is added. The reaction mixture is cooled to −10° C and a solution of 0.29 ml of ethylenechlorophosphite in 3 ml of ethylacetate is added dropwise. After this addition the cooling is removed, and the mixture is stirred for 30 minutes. 498 mg of phenoxyacetic acid are added, and stirring is continued for 2.5 hours at room temperature. The mixture is worked up by shaking twice with ice-cold 1 N hydrochloric acid, twice with cold bicarbonate and once with ice-water. Drying over sodium sulfate and evaporation yields 1.05 g (70%) of an amorphous residue.

The IR spectrum (CHCl$_3$) shows characteristic bands at 1505 cm$^{-1}$ (amide II), 1685 cm$^{-1}$ (amide I), 1750 cm$^{-1}$ (-CO-, ester), and 1785 cm$^{-1}$ (-CO-, β-lactam).

The NMR spectrum (CDCl$_3$) shows signals at:

| δ ppm | | |
|---|---|---|
| 1.20 | | C(CH$_3$)$_2$ |
| 1.52 (s) | | (2) C ⟨CH$_3$ / CH$_3$⟩ |
| 1.60 (s) | | |
| 4.47 (s) | | (3) C—H |
| 4.54 (s) | | φ—O—CH$_2$—CO—NH |
| 5.4–6.0 (m) | J$_{5,6}$ ≈ 4.0 Hz | (5) C—H / (6) C—H / —O—CH$_2$—O— |
| 6.8–7.5 (m) | | φ—O—CH$_2$ |

EXAMPLE 26

2',2',2'-trichloroethyl-3-methyl-7β-(phenoxyacetamido)-ceph-3-em-4-carboxylate 0.61 g (4 millimoles) of phenoxyacetic acid is added to a solution of 2',2',2'-trichloroethyl-3-methyl-7β-(ethylenephosphiteamido)-ceph-3-em-4-carboxylate in acetonitrile prepared as described in Example 12, except for the filtration to remove the precipitate of triethylammonium chloride. The mixture is stirred for 18 hours at room temperature. The reaction mixture is then poured into ice-water and extracted three times with ethylacetate. The combined organic phases are washed three times with 2 N sulfuric acid and three times with saturated sodium hydrogen carbonate solution, dried over MgSO$_4$ and evaporated in vacuum to form an amorphous powder:

Yield: 1.61 g (84%) of 2',2',2'-trichloroethyl-3-methyl-7β-(phenoxyacetamido)-ceph-3-em-4-carboxylate.

The IR spectrum (KBr) shows characteristic bands at 1735 cm$^{-1}$ (-CO-, ester) and 1780 cm$^{-1}$ (-CO-, β-lactam).

The NMR spectrum (DMSO-d$_6$) shows characteristic signals at:

| δ ppm | | |
|---|---|---|
| 2.12 (s) | | (3) —CH$_3$ |
| 3.55 (s) | | (2) —CH$_2$— |
| 4.60 (s) | | —O—CH$_2$—CO— |
| 5.0 and 5.05 (2 d) | | —O—CH$_2$—CCl$_3$ |
| 5.15 (d) | J = 5 Hz | (6) ≡ C—H |
| 5.68 (q) | J = 5 and 8 Hz | (7) ≡ C—H |
| 6.7–7.5 (m) | | —O—φ |

EXAMPLE 28

Benzyl 6-phenoxyacetamidopenicillanate 0.479 g (1 millimol) of benzyl 6-aminopenicillanate, p-toluenesulphonate is dissolved in 2 ml of dry pyridine at 0° C, and a solution of 0.438 ml (0.5 millimol) of PCl$_3$ in 1 ml of dry pyridine is added dropwise within 10 minutes. The temperature is then allowed to raise to room temperature, and the mixture is stirred for further 30 minutes at this temperature. 0.152 g (1 millimol) of phenoxyacetic acid is added to the benzyl 6[N-(3-benzyloxycarbonylpenicillan-6-yl)-phosphazo]-aminopenicillanate solution thus formed, and the mixture is stirred at room temperature for 1 hour. The reaction mixture is poured into 30 ml of ethylacetate and 30 ml of 5% ice-cold aqueous sodium bicarbonate, and the ethylacetate phase is extracted with ice-cold 0.5 N H$_2$SO$_4$ and water. Subsequently, the ethylacetate phase is dried over anhydrous magnesium sulphate and evaporated so as to yield 0.38 g (86%) of a white substance. By IR, NMR and TLC analysis the product is shown to be benzyl 6-phenoxyacetamidopenicillanate.

EXAMPLE 27

Benzyl 6-N-(carbobenzoxy)-D(−)-α-aminophenylacetamidopenicillanate 4.76 g of N-carbobenzoxy-D(−)-phenylglycine in dry methylene chloride at room temperature are added to the product (6.5 g of benzyl 6-ethylenephosphiteamidopenicillanate) of the reaction described in Example 9 under nitrogen. The mixture is stirred for 4 hours, evaporated to dryness, dissolved in 50 ml of ethylacetate and shaken with ice-water (twice), bicarbonate (twice) and finally with ice-water (twice). The solution is dried over magnesium sulfate and evaporated in vacuum to give 1.44 g (75%) of an amorphous substance.

The IR spectrum (CHCl$_3$) shows characteristic bands at 1500 cm$^{-1}$ (amide II), 1690 cm$^{-1}$ (amide I), 1725 cm$^{-1}$ (-CO-, ester), and 1785 cm$^{-1}$ (-CO-, β-lactam).

The NMR spectrum (CDCl$_3$) shows signals at:

| δ ppm | |
|---|---|
| 1.30 (s) <br> 1.45 (s) | }(2) C<CH$_3$ / CH$_3$ \ CH$_3$ |
| 4.40 (s) | (3) C—H |
| 5.05 (s) | NH—CO—O—CH$_2$—φ |
| 5.15 (s) | (3) C—CO—O—CH$_2$—φ |
| 5.4 | { (5) C—H, <br> (6) C—H |
| 7.3 2(s) | 2 × φ |

EXAMPLE 28

2',2',2'-trichloroethyl-3-methyl-7β-[N-(tert-butoxycarbonyl)-D(—)-α-phenylglycylamido]-ceph-3-em-4-carboxylate 1.01 g (4 millimoles) of N-(tert-butoxycarbonyl)-D(—)-α-phenylglycine are added to a solution of 2',2',2'-trichloroethyl-3-methyl-7β-(ethylenephosphiteamido)-ceph-3-em-4-carboxylate in acetonitrile, prepared as described in Example 12, except for the filtration to remove the precipitated triethylammonium chloride. The mixture is stirred for 22 hours. Then the reaction mixture is poured into ice-water and extracted three times with ethylacetate. The combined organic phases are washed three times with 2 N sulfuric acid and three times with saturated sodium hydrogencarbonate solution, dried over MgSO$_4$ and evaporated in vacuum to form an amorphous powder.

Yield: 1.65 g (71%) of 2',2',2'-trichloroethyl-3-methyl-7β-[N-(tert-butoxycarbonyl)-D(—)-α-phenylglycylamido]-ceph-3-em-4-carboxylate.

The IR spectrum (KBr) shows characteristic bands at 1680–1740 cm$^{-1}$ (broad, -CO-, ester and amide) and 1782 cm$^{-1}$ (-CO-, β-lactam).

The NMR spectrum (CDCl$_3$) shows characteristic signals at:

| δ ppm | | |
|---|---|---|
| 1.40 (s) | | —C(CH$_3$)$_3$ |
| 2.17 (s) | | (3) —CH$_3$ |
| 2.9–3.65 (2d) | J = 18 Hz | (2) —CH$_2$— |
| 4.6–5.1 (m) | | —O—CH$_2$—CCl$_3$ and (6) C—H |
| 5.25 (d) | | φ—C—H |
| 5.8 (m) | | (7) C—H and { amide N—H <br> { amide N—H |
| 7.0 (d) | | |
| 7.38 (s) | | φ— |

EXAMPLE 29

Pivaloyloxymethyl 6-D(—)-α-azidophenylacetamidopenicillanate

Method A 1.08 g of pivaloyloxymethyl 6-aminopenicillanate are dissolved in 20 ml of dry methylene chloride under nitrogen, and 0.46 ml of triethylamine is added thereto. The reaction mixture is cooled to —40° C, and a solution of 0.29 ml of ethylenechlorophosphite in 3 ml of dry methylene chloride is added dropwise. When the addition is complete the cooling is removed and the mixture stirred for 30 minutes. Then 0.54 g of D(—)-α-azidophenylacetic acid is added and stirring continued for 18 hours at 0° C. The mixture is worked up by shaking with 30 ml of ice-water (twice), 30 ml of cold 1% bicarbonate (twice) and 30 ml of ice-water (twice). After drying over magnesiumsulfate and evaporation 1.11 g (76%) of pivaloyloxymethyl 6-D(—)-α-azidophenylacetamidopenicillanate is obtained.

The IR spectrum (CHCl$_3$) shows characteristic bands at 1505 cm$^{-1}$ (amide II), 1685 cm$^{-1}$ (amide I), 1755 cm$^{-1}$ (-CO-, ester), 1785 cm$^{-1}$ (-CO-, β-lactam), 2110 cm$^{-1}$ (azide), and 3380 cm$^{-1}$ (amide-NH).

The NMR spectrum (CDCl$_3$) shows signals at:

| δ ppm | |
|---|---|
| 1.2 (s) | C(CH$_3$)$_3$ |
| 1.52 (s) <br> 1.65 (s) | }(2) C<CH$_3$ / \ CH$_3$ |
| 4.45 (s) | (3) C—H |
| 5.10 (s) | CO— / φ—CH \ N$_3$ |
| 5.5–6.0 (m) | { (5) C—H, <br> { (6) C—H <br> —O—CH$_2$—O— |
| 7.37 (s) | φ— |

Method B

The procedure described under method A was followed, except that 0.41 ml of diethylchlorophosphite was used instead of 0.29 ml of ethylenechlorophosphite. Yield: 1.02 g (70%) of pivaloyloxymethyl 6-D(—)-α-azidophenylacetamidopenicillanate.

The IR and NMR spectra show the same characteristic signals as those of the product prepared according to method A.

Method D 10.6 g of 6-aminopenicillanic acid are dissolved in 75.0 ml of acetonitrile by addition of 16.0 ml of triethylamine, and the solution formed is cooled to −40° C. A solution of 4.6 ml of ethylenechlorophosphite in 25.0 ml of acetonitrile cooled to −40° C is added in one portion while stirring and introducing dry nitrogen. After stirring for ½ hour, during which period the temperature gradually raises to room temperature, the triethylammonium chloride is removed by filtration.

0.7 ml of triethylamine and 10.0 ml of chloromethylpivalate are added to the solution obtained while introducing dry nitrogen, and the mixture is stirred for 18 hours.

After removal of the triethylammonium chloride formed by filtration the filtrate is cooled to 0° C, and 12.4 g of D(−)-α-azidophenylacetic acid are added. After standing for 22 hours at 0° C the solution is poured into 400 ml of 2% ice-cold $NaHCO_3$ solution. The mixture is extracted with ethylacetate, and after separation of the phases the aqueous phase is extracted once more with ethylacetate. The combined ethylacetate phases are washed with water, dried over $Na_2SO_4$ and evaporated in vacuum to dryness at a low temperature to give 18.0 g of a residue. The IR and NMR spectra of said residue show the same characteristic signals as those of the product prepared according to method A.

EXAMPLE 30

Phthalidyl 6-[D(−)-α-aminophenylacetamido]penicillanate, hydrochloride

A solution of the triethylammonium salt of 6-ethylene phosphite amidopenicillanic acid was prepared from 2.16 g (10 millimoles) of 6-aminopenicillanic acid in the manner described in Example 1 and the triethylammonium chloride formed was removed by filtration.

The NMR spectrum ($CH_3CN$) of a sample of the reaction solution showed that all 6-aminopenicillanic acid had been converted into the corresponding ethylene phosphiteamido compound, and the following characteristic signals were obtained:

| δ ppm | | |
|---|---|---|
| 3.98 (s) | | (3) C—H |
| 4.86 (multiplet consisting of 8 peaks) | | |
| $J_{HCCH}$ = 4.2 Hz, | $J_{HNCH}$ = 6.3 Hz | |
| $J_{PNCH}$ = 11.8 Hz | | (6) C—H |
| 5.40 (d) | $J_{HCCH}$ = 4.2 Hz | (5) C—H |

The solution formed was cooled to 10° C and 2.13 g (10 millimoles) of 3-bromophthalide were added.

After 2 hours the NMR spectrum ($CH_3CN$) showed that the reaction was completed, thus:

| in bromophthalide: | |
|---|---|
| δ ppm | |
| 7.65 (s) | (3) C—H has disappeared |
| while in | |
| the ester compound: | |
| δ ppm | |
| 7.45 (s) | for the corresponding proton ~ 1 H |

Furthermore, the NMR spectrum shows the following characteristic signals:

| δ ppm | | |
|---|---|---|
| 4.46 (s) | | (3) C—H |
| 5.00 (multiplet consisting of 8 peaks) | | |
| $J_{HCCH}$ = 4.5 Hz, | $J_{HNCH}$ = 6.3 Hz | |
| $J_{PNCH}$ = 11.7 Hz | | (6) C—H |
| 5.43 (d) | $J_{HCCH}$ = 4.5 Hz | (5) C—H |

This solution of phthalidyl 6-ethylene phosphiteamidopenicillanate is cooled to 0° C, whereafter 2.06 g (10 millimoles) of D(−)-phenylglycyl chloride hydrochloride are added in portions during a period of 5 minutes.

After stirring at 0° C for 2 hours, the reaction mixture is poured into 50 ml cold saturated aqueous NaCl solution. 30 ml ethyl acetate are added and the mixture is stirred for 15 minutes while being subjected to ice cooling. After phase separation the organic phase is further washed with cold saturated NaCl solution, dried over $MgSO_4$ and evaporated to dryness in vacuum so as to obtain a solid residue.

After treatment with ether, the residue is converted to a crystalline substance which after drying in vacuum weighs 3.9 g and has a melting point of 175°–180° C (d). Yield: 70% dihydrate, purity: 96.5%.

Analysis of a product dried for 20 hours at 0.005 mm Hg at room temperature:

Calculated for $C_{24}H_{26}O_7ClN_3S$: C = 54.3%, H = 4.83%, Cl = 6.54%, N = 7.76%, S = 5.92%.

Found: C = 53.0%, H = 4.85%, Cl = 6.31%, N = 7.96%, S = 6.37%.

The IR spectrum (KBr) shows characteristic bands at 1779 $cm^{-1}$ (-CO-β-lactam and ester), 1681 $cm^{-1}$ and 1492 $cm^{-1}$ (-CONH I and II).

The NMR spectrum ($DMSO-d_6/D_2O$) shows characteristic signals at:

| δ ppm | | |
|---|---|---|
| 1.43 (d) | | $\diagup CH_3$ |
| | | (2) C |
| | | $\diagdown CH_3$ |
| 4.52 (s) | | (3) C—H |
| 5.10 (s) | | $C_6H_5$—CH |
| | | \|— |
| | | $NH_2$ |
| 5.50 (2 d) | $J_{HCCH}$ = 4.2 Hz | { (5) C—H |
| | | { (6) C—H |
| 7.49 (s) | | $C_6H_5$— |
| 7.56 (s) | | COOCH |
| | | \|— |
| 7.89 (m) | | $C_6H_4$ |

EXAMPLE 31

Phthalidyl
7-[D(−)-α-aminophenyl-acetamido]-desacetoxycephalosporanate, hydrochloride 4.28 g (20 millimoles) of 7-aminodesacetoxycephalosporanic acid are slurried in 40 ml dry acetonitril. The slurry is cooled under dry nitrogen to −40° C and 5.6 ml (40 millimoles) of triethylamine are added. 1.8 ml (20 millimoles) of ethylenechlorophosphite dissolved in 4 ml dry acetonitril are added dropwise. This addition causes the temperature to raise to −25° C. The reaction mixture is slowly heated to 25° C. After a period of 20 minutes the mixture is cooled to 5° C and 4.24 g (20 millimoles) of bromophthalide are added. The mixture thus obtained is stirred at 10° C for 3 hours. After cooling to 5° C 4.1 g (20 millimoles) of D(−)-phenylglycylchloride, hydrochloride are added. The temperature raises to 10° C. Stirring is continued for additionally 2.5 hours at room temperature.

80 ml methylenechloride are added to the reaction mixture and the mixture thus obtained is poured into 100 ml cold saturated sodiumchloride solution. The washing is repeated twice with 30 ml sodiumchloride solution. The organic phase is extracted four times with 25 ml of water. The combined water phases are extracted twice with 40 ml of ethylacetate, whereafter the water phases are evaporated to dryness.

After drying for 20 hours over phosphorpentaoxide 4.3 g of phthalidyl 7-[D(−)-α-aminophenyl-acetamido]-desacetoxycephalosporanate, hydrochloride of high purity are obtained.

The IR spectrum (KBr) shows characteristic bands at 1750–1790 cm$^{-1}$ (β-lactam and ester), 1690 cm$^{-1}$ (amide I), 1605 cm$^{-1}$ (double bond) and 1500 cm$^{-1}$ (amide II).

| Analysis: Calculated for | C | H | N | S |
|---|---|---|---|---|
| $C_{24}H_{24}N_3ClO_7S$: | 53.99% | 4.53% | 7.87% | 6.00% |
| Found: | 54.57% | 4.83% | 7.98% | 5.90% |

EXAMPLE 32

Phthalidyl
7-[D(−)-α-amino-phenyl-acetamido]-cephalosporanate, hydrochloride 2.71 g (10 millimoles) of 7-aminocephalosporanic acid are dissolved in 20 ml dry acetonitril by addition of 1.82 ml (13 millimoles) of triethylamine, and subsequently the mixture is cooled to −40° C in a dry nitrogen atmosphere. After addition of 0.9 ml (10 millimoles) of ethylenechlorophosphite dissolved in 2.5 ml dry acetonitril an additional amount of 0.84 ml (6 millimoles) of triethylamine is added. The temperature is allowed to raise to 0° C over a period of 1.3/4 hour. The precipitated triethylammoniumchloride is separated by filtration under dry nitrogen, and 2.13 g (10 millimoles) of 3-bromophthalide dissolved in 5 ml dry acetonitril are added dropwise. The temperature is raised to 10° C, and stirring is continued for further 2 hours. The temperature is lowered to 0° C and 2.06 g (10 millimoles) of D(−)-phenylglycylchloride, hydrochloride are added in portions. The stirring is continued for 1½ hour at 0° C, and the reaction mixture is then poured into an ice-cold mixture of 50 ml saturated aqueous NaCl solution and 25 ml ethylacetate. Stirring is continued for further 15 minutes, and the phases are separated. The organic phase is shaken with saturated NaCl solution, dried over MgSO$_4$ and evaporated to dryness. When treated with dry ether, the residue becomes solid, and after filtration 3.93 g (68%) of the product are obtained.

The NMR spectrum shows that the product obtained consists of 7-[D(−)-α-aminophenylacetamido]-cephalosporanate, hydrochloride containing 20–25% of the Δ$^2$ isomeric compound. When DMSO-d$_6$ is used as a solvent and TMS as internal standard, the following characteristic signals are obtained:

| | |
|---|---|
| δ 9.63 ppm | (1H, d, J = 7.5 Hz, —CONH) |
| δ 8.9 ppm | (3H, broad s, —N$^+$H$_3$) |
| δ 7.85 ppm | (4H, m, aromatic phthalide) |
| δ 7.69 ppm | (1H, m, aliphatic phthalide) |
| δ 7.49 ppm | (5H, s, C$_6$H$_5$—) |
| δ 5.7 ppm | (1H, m, (7) C—H) |
| δ 5.2–4.5 ppm | (4H, m, (6) C—H, α—C—H, >C—CH$_2$—OC—O) |
| δ 3.53 ppm | (2H, broad s, S\CH$_2$) |
| δ 1.98 ppm | (3H, m, —OCOCH$_3$) |

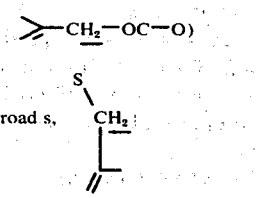

After addition of D$_2$O the δ9.63 and δ8.9 signals disappear, whereas the δ5.7 signal is converted to δ5.73 (1H, d, J = 4.6 Hz). When using CD$_3$CN/D$_2$O as solvent and TMS as internal standard, the δ5.2–4.5 multiplet is dissolved so that the NMR spectrum within the range δ5.8–4.5 gets the following characteristics:

| | |
|---|---|
| δ 5.72 ppm | (1H, d, J = 4.6 Hz) |
| — 5.17 — | (1H, s) |
| — 4.99 — | (1H, d, J = 14 Hz) |
| — 4.97 — | (1H, d, J = 4.6 Hz) |
| — 4.70 — | (1H, d, J = 14 Hz) |

The (7) CH of the Δ$^2$ isomer is seen at δ5.55 ppm (d, J = 4.2 Hz).

The IR spectrum (KBr) has i.a. strong bands at 1785 cm$^{-1}$, 1745 cm$^{-1}$ and 1695 cm$^{-1}$.

In order to analyze the product it was converted into a perchlorate by precipitation from water with perchloric acid. After precipitation from butylacetate with ether a partially crystalline product is obtained. The product has a melting point (d) at 132° C and binds ½ mole butylacetate after drying in vacuum (0.05 mm Hg).

Analysis: Calculated based on $C_{29}H_{30}N_3O_{13}SCl$: C: 50.15, H: 4.35, N: 6.04, S: 4.61, Cl: 4.96%, Found: C: 49.63, H: 4.32, N: 6.12, S: 4.89, Cl: 4.87%.

EXAMPLE 33

Phthalidyl 7-(2-thienylacetamido)-cephalosporanate 0.81 g (3 millimoles) of 7-aminocephalosporanic acid is slurried in 5 ml dry acetonitril at room temperature and is dissolved by the addition of 0.84 ml (6 millimoles) of triethylamine. The solution is cooled to −40° C in a dry nitrogen atmosphere, and subsequently 0.27 ml (3 millimoles) of ethylenechlorophosphite is added. The temperature is allowed to raise to 0° C over a period of 30 minutes. When the precipitated triethylammoniumchloride has been removed by filtration, 0.64 g (3 millimoles) of 3-bromophthalide dissolved in 2.5 ml dry acetonitril is added. The reaction mixture is stirred while the temperature raises to 10° C over a period of 1.3/4 hour. The mixture is then cooled to 0° C, and 3 millimoles of 2-thienylacetylchloride dissolved in 2.5 ml dry acetonitril are added dropwise.

The mixture is stirred for 1½ hour at 0° C and is subsequently poured into 20 ml of an ice-cold saturated aqueous NaCl solution covered by 10 ml ethylacetate. After stirring for 15 minutes, the phases are separated and the organic phase is shaken with ice-cold saturated NaCl solution, dried over $MgSO_4$ and evaporated in vacuum. A dark, oily residue thus obtained is dissolved in 10 ml butylacetate. The solution is filtered, and the filtrate is stirred with 10 ml water, whereafter the pH-value of the water phase is adjusted at 6.5 with diluted NaOH. The phases are separated, and the organic phase is shaken with water, dried over anhydrous $MgSO_4$ and evaporated in vacuum to form 6.4 g of a light solid crude product. TLC: One $J_2$/starch reducing spot.

The product is purified by repeated precipitations from ethylacetate with ether, and 3.4 g corresponding to 54% of the theoretical yield are obtained. NMR shows that the product obtained contains 10–15% of the $\Delta^2$ isomer.

The NMR spectrum in DMSO-$d_6$ and TMS as internal standard has characteristic signals at:

| | |
|---|---|
| δ 9.10 ppm | (1H, d, J = 7 Hz, —CON__H__—) |
| δ 7.85 ppm | (4H, m, aromatic phthalide) |
| δ 7.69 ppm | (1H, m, aliphatic phthalide) |
| δ 7.39 ppm | (1H, t- H—C) |
| δ 6.96 ppm | (2H, d, CH—CH) |
| δ 5.74 ppm | (1H, m, (7) —C—__H__) |
| δ 5.12 ppm | (1H, d, J = 4.5 Hz, (6) C—__H__) |
| δ 5.06 ppm | (1H, d, J = 14 Hz, —C—OCO—) |
| δ 4.75 ppm | (1H, d, J = 14 Hz, —C—OCO—) |
| δ 3.76 ppm | 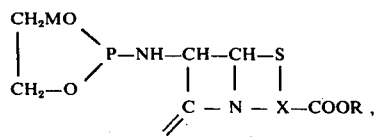 (2H, s, —C__H_2__—CO—) |
| δ 3.65 ppm | (2H, broad s, C__H_2__) |
| δ 2.00 ppm | (3H, m, —OCO—C__H_3__) |

After addition of $D_2O$ the signal at δ9.10 ppm disappears, and (7) C-H is converted into δ5.70 ppm (1H, d, J = 4.5 Hz). It appears from the spectrum that (7) C-H of the $\Delta^2$ isomer produces a signal at δ5.49 ppm (d, J = 4.2 Hz) and based on the ratio between the integrals of the two (7) C-H of the two isomers it can be seen that the $\Delta^2$ isomer constitutes 13% of the product.

The IR spectrum (KBr) shows i.a. strong bands at 1785 $cm^{-1}$, 1740 $cm^{-1}$ and 1685 $cm^{-1}$.

What we claim is:

1. Novel intermediates for the preparation of penicillins and cephalosporins and derivatives thereof characterized by the general formula:

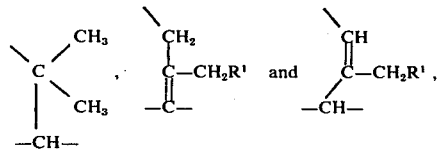

wherein X is selected from the group consisting of $$\begin{array}{ccc} \diagdown\diagup^{CH_3}_{CH_3} & \diagdown_{C-CH_2R^1}^{CH_2} & \diagdown_{CH-}^{CH}C-CH_2R^1 \\ | & \| & \diagup \\ -CH- & -C- & \end{array}$$

wherein R is selected from the group consisting of diethylammonium, triethylammonium, trimethylsilyl and phthalidyl, wherein $R^1$ is a hydrogen atom or an acetoxy group.

2. The intermediate according to the formula of claim 1 identifiable as 6-ethylenephosphiteamidopenicillanic acid, triethylammonium salt.

3. The intermediate according to the formula of claim 1 identifiable as trimethylsilyl-6-ethylenephosphiteamidopenicillanate.

4. The intermediate according to the formula of claim 1 identifiable as phthalidyl-6-ethylenephosphiteamidopenicillanate.

* * * * *

UNITED STATES PATENT OFFICE
CERTIFICATE OF CORRECTION

Patent No. 3,994,883                     Dated November 30, 1976

Inventor(s) Borrevang, Guddal, Petersen, Faarup, Nielsen

It is certified that error appears in the above-identified patent and that said Letters Patent are hereby corrected as shown below:

Column 38, lines 33-43, should read

-. Novel intermediates for the preparation of penicillins and cephalosporins and derivatives thereof characterized by the general formula:

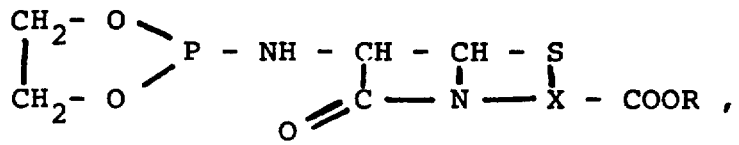

wherein X is selected from the group consisting of --,

Signed and Sealed this

Twenty-seventh Day of December 1977

[SEAL]

Attest:

RUTH C. MASON  
Attesting Officer

LUTRELLE F. PARKER  
Acting Commissioner of Patents and Trademarks